United States Patent
Nemeh et al.

(10) Patent No.: US 11,517,215 B2
(45) Date of Patent: Dec. 6, 2022

(54) METHODS AND APPARATUS FOR ELECTRO-MERIDIAN DIAGNOSTICS

(71) Applicant: Ninurta Inc., Westlake, OH (US)

(72) Inventors: Issam Nemeh, Westlake, OH (US);
Todd Quinn, Elyria, OH (US);
Deborah Nemeh, Westlake, OH (US);
Wadi Nemeh, Westlake, OH (US);
Andreas Mershin, Arlington, MA (US)

( * ) Notice: Subject to any disclaimer, the term of this patent is extended or adjusted under 35 U.S.C. 154(b) by 300 days.

(21) Appl. No.: 16/836,806

(22) Filed: Mar. 31, 2020

(65) Prior Publication Data

US 2022/0354379 A1 Nov. 10, 2022

Related U.S. Application Data

(60) Provisional application No. 62/828,206, filed on Apr. 2, 2019.

(51) Int. Cl.
| | |
|---|---|
| *A61B 5/0532* | (2021.01) |
| *A61B 5/00* | (2006.01) |
| *G16H 70/60* | (2018.01) |
| *G16H 50/20* | (2018.01) |

(52) U.S. Cl.
CPC .......... *A61B 5/0532* (2013.01); *A61B 5/7282* (2013.01); *G16H 50/20* (2018.01); *G16H 70/60* (2018.01)

(58) Field of Classification Search
CPC ..... A61B 5/053; A61B 5/0531; A61B 5/0532; A61B 5/7282; G16H 50/20; G16H 70/60
See application file for complete search history.

(56) References Cited

U.S. PATENT DOCUMENTS

| | | | |
|---|---|---|---|
| 3,971,366 A * | 7/1976 | Motoyama | A61B 5/0531 600/384 |
| 4,940,060 A | 7/1990 | Gu et al. | |
| 5,339,827 A * | 8/1994 | Masopust | A61B 5/0532 600/548 |
| 6,285,905 B1 | 9/2001 | Chiang et al. | |
| 6,735,469 B2 | 5/2004 | Lee et al. | |

(Continued)

OTHER PUBLICATIONS

Amaro, J., Electro-Meridian Imaging: Case Histories; published in Acupuncture Today, vol. 03, Issue 11, Nov. 2002.

(Continued)

*Primary Examiner* — Franklin D Balseca
(74) *Attorney, Agent, or Firm* — Smith Keane LLP

(57) ABSTRACT

A current sensor may take measurements of electrical currents that flow between two limbs of a patient through at least a portion of the patient's torso. The current measurements may be taken during a single diagnostic session while the patient holds a ground electrode in a hand of one limb and a probe electrode is sequentially placed at different locations on the distal portions of other limbs. Each of the measurement locations may be an acupuncture point. An electrical current state for the diagnostic session may be calculated. This state may consist of current ranges for one or more electrical currents that are measured during the session. A lookup table may be employed to determine one or more medical conditions that are indicated by the current state. Alternatively, a trained machine learning model may predict, based on the measured currents, one or more medical conditions.

20 Claims, 9 Drawing Sheets

(56) References Cited

U.S. PATENT DOCUMENTS

| | | | |
|---|---|---|---|
| 6,934,581 B2* | 8/2005 | Kanevsky | A61B 5/0532 600/547 |
| 2015/0057574 A1 | 2/2015 | Baym et al. | |
| 2021/0219860 A1 | 7/2021 | Garff et al. | |

OTHER PUBLICATIONS

Chang, S., et al., Application of Meridian Electrical Conductance in the Setting of Acute Ischemic Stroke: A Cross-Sectional Study; published in Evidence-Based Complementary and Alternative Medicine, vol. 2019, Article ID 3098095, Aug. 14, 2019.

Gervais, D., et al., Rule-based AI for acupuncture treatment using microcomputers; published in Journal of the Indian Institute of Science, vol. 67, pp. 491-503 (1987).

Mist, S., et al., Reliability of AcuGraph system for measuring skin conductance at acupoints; published in Acupuncture in Medicine, 2011; 29(3): 221-226 (May 2011).

Nakatani, Y., et al., A Guide for Application of Ryodoraku Autonomous Nerve Regulatory Therapy; published in Ryodoraku Medicine and Stimulus Therapy, vol. 1, pp. 1-20, 2018.

Spaulding, K., et al., The Transport of Extremely Low-Frequency Electrical Signals Through an Acupuncture Meridian Compared to Nonmeridian Tissue; published in The Journal of Alternative and Complementary Medicine, vol. 17, No. 2, pp. 127-132 (2011).

Wong, Y., Skin Resistance Measurement in Japanese Acupuncture, vol. 42, Issue 4, pp. 161-162 (2014).

Zhang, G., et al., Machine learning methods for improving acupuncture data consistency: a review; published in OA Alternative Medicine, 2(1):5 (Mar. 2014).

Zhao, C., et al., Advances in Patient Classification for Traditional Chinese Medicine: A Machine Learning Perspective published in Evidence-Based Complementary and Alternative Medicine, 2015: 376716 (2015).

International Search Report for Application No. PCT/US 22/35418, dated Oct. 5, 2022, 2 pages.

Written Opinion of ISA for Application No. PCT/US 22/35418, dated Oct. 5, 2022, 5 pages.

\* cited by examiner

METHODS AND APPARATUS FOR ELECTRO-MERIDIAN DIAGNOSTICS

RELATED APPLICATIONS

This application claims the benefit of U.S. Provisional Application No. 62/828,206 filed Apr. 2, 2019 (the "Provisional").

SUMMARY

In illustrative implementations, a diagnostic system employs a current sensor to screen for and to detect a wide variety of medical conditions. The current sensor may take measurements of small electrical currents that flow between a probe electrode and a ground electrode, while a patient holds the ground electrode in one hand and the probe electrode is sequentially placed at different locations on the patient's two feet and on the patient's other forearm. These cross-body currents may flow through at least a portion of the patient's torso. The ground electrode may be switched from one hand to another, to enable current measurements to be taken for both forearms.

The measurements of electrical current may be taken during a single diagnostic session. Each of the measurement locations may be an acupuncture point.

Based on the measurements, an electrical current state for the diagnostic session may be calculated. This state may consist of: (a) a current range for an electrical current that is measured during the session; or (b) current ranges for respective currents that are measured during the session. A lookup table may be employed to determine one or more medical conditions that are indicated by the current state. Alternatively, a trained machine learning model may predict, based on the measured currents, one or more medical conditions.

In some cases, the diagnostic system determines whether or not a patient has a viral infection and whether or not a patient has a bacterial infection, based on electrical current measurements that take only a few minutes. This ability to quickly and accurately detect and differentiate between viral and bacterial infections enables the diagnostic system to be used as a mass-scale, rapid screening tool in a viral or bacterial epidemic. For instance, during the COVID-19 pandemic, the diagnostic tool may be used to quickly determine whether a patient has a viral or bacterial infection or both, and if a viral infection is indicated, to refer the patient for a panel of respiratory virus tests, including a COVID-19 assay.

In some cases, the ground electrode and probe electrode are attached to flexible wires and are free to move relative to each other.

Alternatively, in some cases, the ground electrode and probe electrode are rigid parts of a single rigid structure and thus are in a fixed position relative to each other. The rigid structure may be configured to also serve as a case for a smartphone. The rigid structure may enable a patient to hold both the probe electrode and ground electrode in one hand. For instance, the patient may hold the rigid structure in such a way that the ground electrode of the rigid structure is pressed against the palm of one hand, while the patient sequentially presses the probe electrode at different points on the patient's left foot, right foot and other forearm.

In some cases, one or more pressure sensors measure how much pressure is being applied to the probe and/or ground electrodes. These pressure readings, as well as current readings by the current sensor, may be employed to determine whether the electrodes are being pressed properly against the patient's skin to achieve sufficient conductance for accurate measurements. In some cases, the ground electrode and probe electrode are rigid parts of a single rigid structure and thus are in a fixed position relative to each other, except for any movement that is due solely to displacements that occur within one or more pressure sensors.

A user interface (UI) may present to a user: (a) information about the measurements; (b) a diagnosis or tentative diagnosis; and/or (c) a recommendation for further medical testing. In addition, the UI may provide real-time audiovisual feedback to a user regarding whether the electrodes are being used properly.

The Summary and Abstract sections and the title of this document: (a) do not limit this invention; (b) are intended only to give a general introduction to some illustrative implementations of this invention; (c) do not describe all of the details of this invention; and (d) merely describe non-limiting examples of this invention. This invention may be implemented in many other ways. Likewise, the Field of Technology section is not limiting; instead it identifies, in a general, non-exclusive manner, a field of technology to which some implementations of this invention generally relate.

The above Figures are not necessarily drawn to scale. The above Figures show illustrative implementations of this invention, or provide information that relates to those implementations. The examples shown in the above Figures do not limit this invention. This invention may be implemented in many other ways.

DETAILED DESCRIPTION

Current Sensor

In illustrative implementations of this invention, a current sensor measures what we sometimes call "cross-body" electrical currents. In some cases, the cross-body currents are electrical currents that flow between distal regions of two limbs of a patient, passing through at least a portion of the patient's torso. In some use scenarios, the current sensor measures a cross-body electrical current that flows between: (a) skin on a patient's hand; and (b) skin on a foot or ankle of the patient. In other use scenarios, the current sensor measures a cross-body electrical current that flows between: (a) skin of a hand of a patient's forearm; and (b) skin of a hand or wrist of the patient's other forearm. In each of the preceding examples, the cross-body electrical current may flow through at least a portion of the patient's torso. In some use scenarios, the current sensor measures cross-body electrical currents that pass through the sagittal plane and/or transpyloric plane of the patient's body.

In some use scenarios, the cross-body electrical currents are very small in magnitude. For instance, in some cases, these electrical currents are in a range from 0.1 microamperes to 500 microamperes, or in a range from 0.1 microamperes to 300 microamperes. In some implementations, the current sensor measures cross-body currents while: (a) a patient holds a ground electrode; and (b) a probe electrode is positioned at different locations on the patient's skin. For instance, cross-body currents may be measured while the probe electrode is located at 24 different locations on the patient's limbs, one location at a time. The 24 measurement locations may consist of: (a) six locations on the right foot and six corresponding locations on the left foot; and (b) six locations on the right hand (or right wrist) and six corresponding locations on the left hand (or left wrist).

In some cases, the current sensor has ground and probe electrodes that are not in a fixed position relative to each other. Put differently, in some cases, the ground and probe electrodes are free to move relative to each other.

Figure 1:
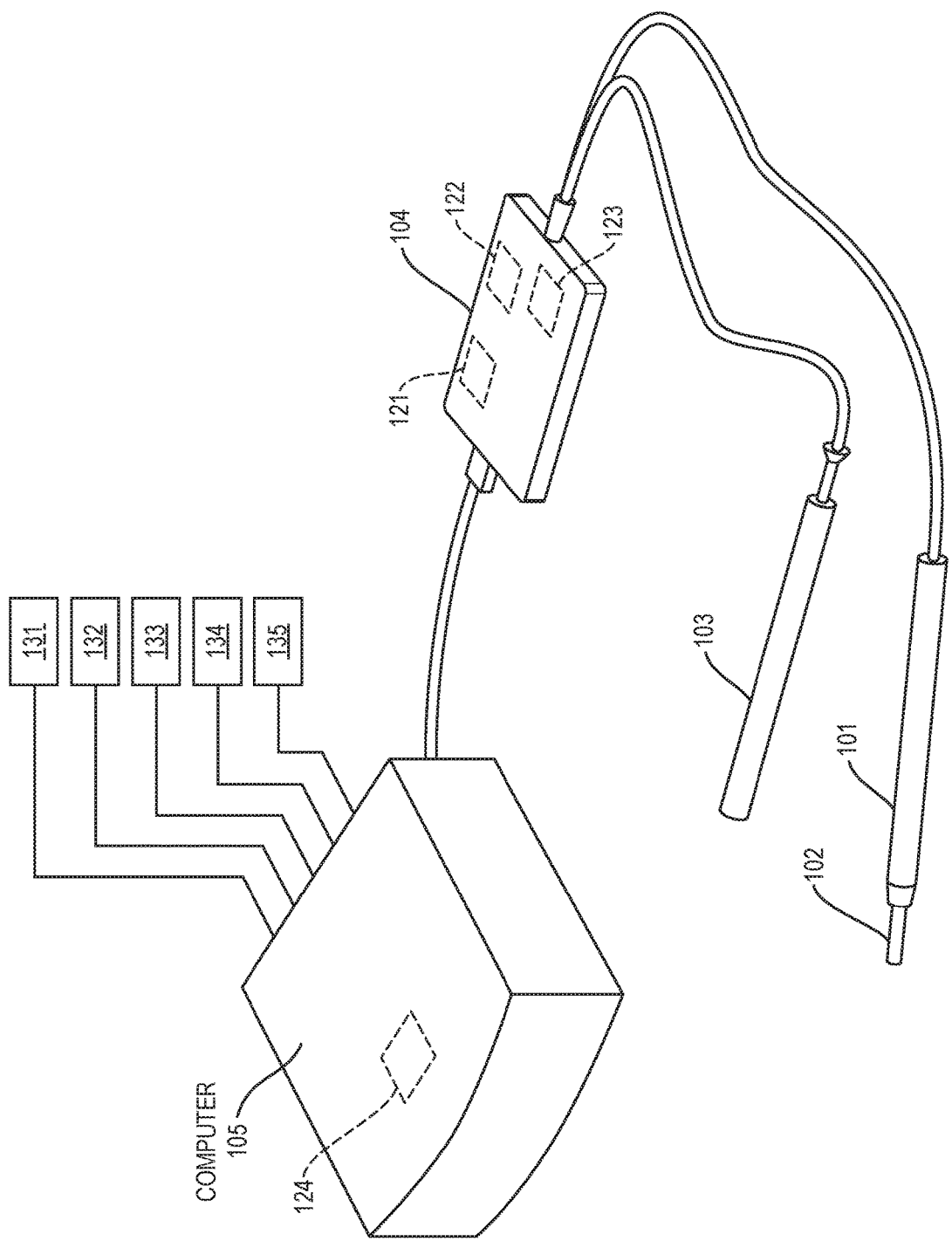
FIG. 1 shows a current sensor which has ground and probe electrodes that are free to move relative to each other.

FIG. 1 shows a current sensor which has ground and probe electrodes that are not in a fixed position relative to each other. In FIG. 1, a current sensing system includes a ground electrode 103, a probe electrode 101, and module 104. The ground and probe electrodes are each connected to flexible wires and may move relative to each other. Ground electrode 103 is configured to be held by a patient directly against the skin of the patient's hand, while the current sensor measures cross-body currents that flow through the patient. Probe electrode 101 has a conductive tip 102 that is configured to be pressed directly against the patient's skin at each of multiple measurement points, one measurement location at a time. The main body of probe electrode 101 (other than conductive tip 101) may be covered by a thin insulative sheath.

In FIG. 1, wires may electrically connect the ground and probe electrodes with module 104. Module 104 may house (among other things) power circuitry 123, ammeter 122 and a microprocessor 121. The power circuitry 123 may include a power source, a (non-ideal) current source or a (non-ideal) voltage source or may otherwise generate or modulate a cross-body electrical current. Power circuitry 123 may in turn receive power from computer 105.

The cross-body electrical currents (which are generated by the power circuitry 123 and that flow between the ground and probe electrodes through a patient's body) may be either DC currents (direct currents) or AC currents (alternating currents). In some cases, microprocessor 121 includes a signal generator. This signal generator: (a) may comprise an oscillator, function generator, waveform generator, or digital pattern generator; and (b) may be employed to control timing and duration of a DC or AC cross-body current.

In FIG. 1, ammeter 122 may comprise any type of current sensor or ammeter, including any type of digital ammeter. For instance, ammeter 122 may employ a shunt resistor to produce an analog voltage that is proportional to current and this voltage may in turn be measured by a digital voltmeter, which employs an ADC (analog-to-digital converter) to convert analog voltage to digital data. In some cases, ammeter 122 includes a current sense amplifier, which comprises a differential amplifier with a matched resistive gain network that monitors current flow by measuring current drop across a sense element, such as a shunt resistor. The current sense amplifier may include an integrated current-sense resistor. In some other cases, ammeter 122 comprises a Hall effect current sensor, transformer current sensor, current clamp sensor, fluxgate transformer current sensor, moving coil ammeter, moving magnet ammeter, or electrodynamic ammeter. Ammeter 122 may produce an analog voltage that is calibrated to be proportional to current, and an ADC may convert this analog voltage to digital data.

In FIG. 1, ammeter 122 may output digital data that represents measurements of cross-body electrical currents that are taken at different points on the patient's limbs. Microprocessor 121 may analyze this digital data.

In FIG. 1, computer 105 controls and interfaces with microprocessor 122, and may further analyze data. Computer 105 may store data in, and access data from, a memory device 124. Computer 105 may interface with a set of input/output (I/O) devices, including a microphone 131, speaker 132, electronic display screen 133 (e.g., a touch screen, computer monitor, or laptop screen), keyboard 134 and mouse 135.

In some use scenarios, a health-care worker holds probe electrode 101 and presses it against different points in the patient's skin, while the patient holds ground electrode 103. At each of the measurement locations, a cross-body electrical current may be measured. For instance, while the patient holds the ground electrode 103 in the palm of one hand with fingers curling around the ground electrode, the health-care worker may hold probe electrode 101 and press it against a sequence of 24 locations on the patient's body, one location at a time. As a non-limiting example, the health-care worker may first press probe electrode 101 against six locations on the patient's right foot, then against six locations on the patient's left foot, then against six locations on the user's right hand or wrist, and then against six locations on the user's left hand or wrist. The current sensor may measure cross-body currents that flow when the probe electrode is at each of these different measurement locations.

Figure 2:
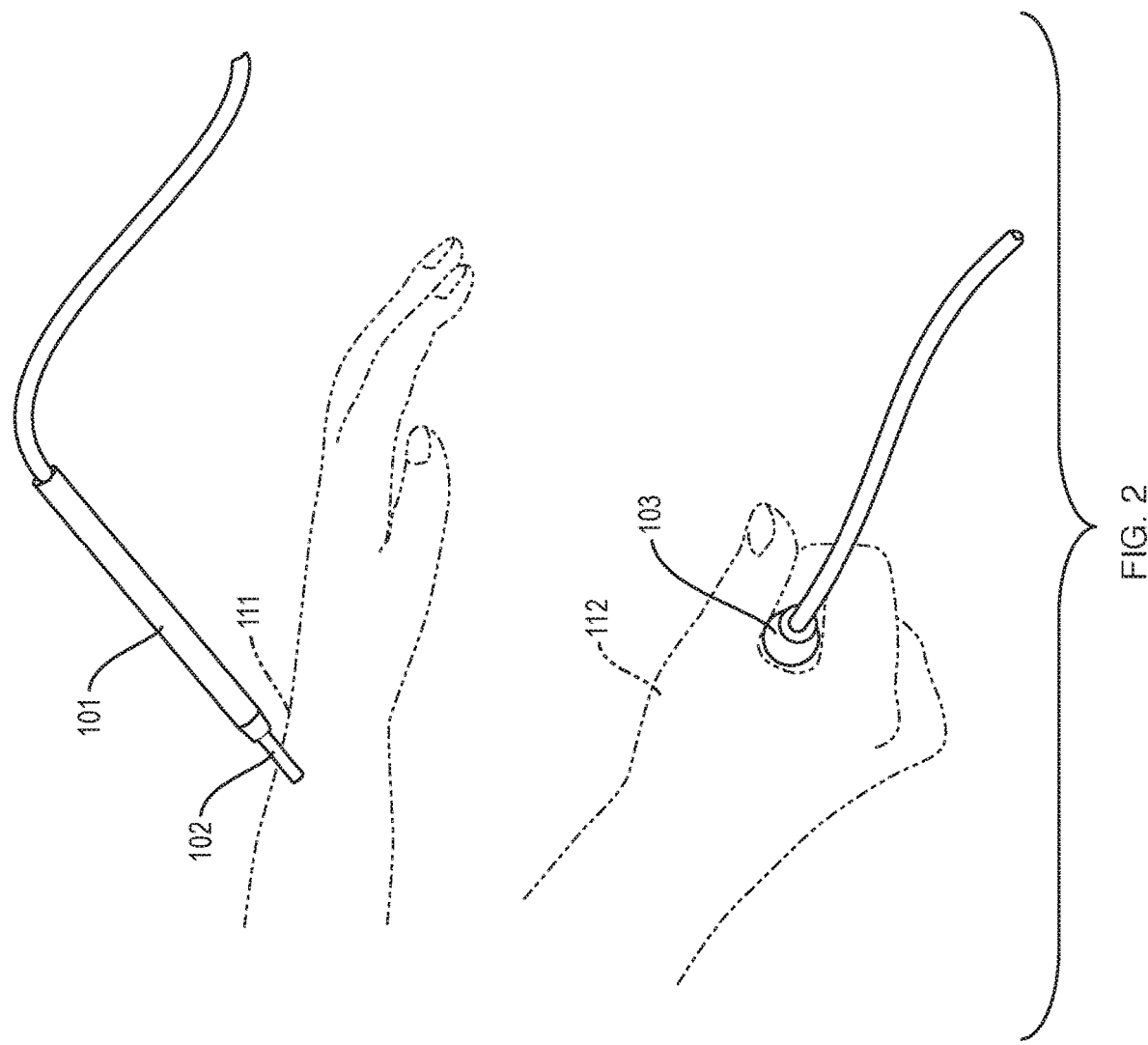
FIG. 2 shows electrodes of a current sensor being employed to measure cross-body electrical currents.

In the example shown in FIG. 2, a health care worker may administer the diagnostic test to a patient. Specifically, in FIG. 2: (a) a patient may hold ground electrode 103 in the palm of a hand 112 with fingers gripping and wrapped around the ground electrode; while (b) a health care worker (not shown) presses the conductive tip 102 of probe electrode 101 against the skin of the patient's other forearm 111.

In some use scenarios, a patient may self-administer at least a portion of the diagnostic test. For instance, while the patient holds the ground electrode 103 in one hand, the patient may hold probe electrode 101 in the other hand and may press it against six locations in the patient's right foot and six locations in the patient's left foot.

However, the apparatus shown in FIG. 1 is not well-suited for a patient himself or herself to take measurements of cross-body currents that occur at hand or wrist measurement points. This is because it can be difficult for the patient to hold the ground electrode and probe electrode in the same hand while pressing the probe electrode against the hand or wrist of the patient's other forearm. When the patient grips the ground electrode in the palm of a hand (with fingers wrapped around the ground electrode), it may be difficult for the patient to also hold the probe electrode in the fingers of the same hand.

In some implementations of this invention, this problem is solved by employing a current sensor in which the ground electrode and probe electrode are parts of a single rigid structure and thus are in a fixed position relative to each other. The patient may hold the rigid structure in one hand, with the ground electrode portion of the rigid structure pressed against the palm of that hand, while pressing the probe electrode portion of the rigid structure against the skin of another extremity. For instance, a user may hold the rigid structure in the right hand with the ground electrode pressed against the skin of the right hand, while pressing the probe electrode first against six locations on the right foot, then against six locations on the left foot, and then against six locations on the left hand. Then the user may hold the rigid structure in the left hand, while pressing the probe electrode portion of the rigid structure against six locations on the right hand. At each of the different measurement locations, the current sensor may measure a cross-body electrical current.

Figure 3:
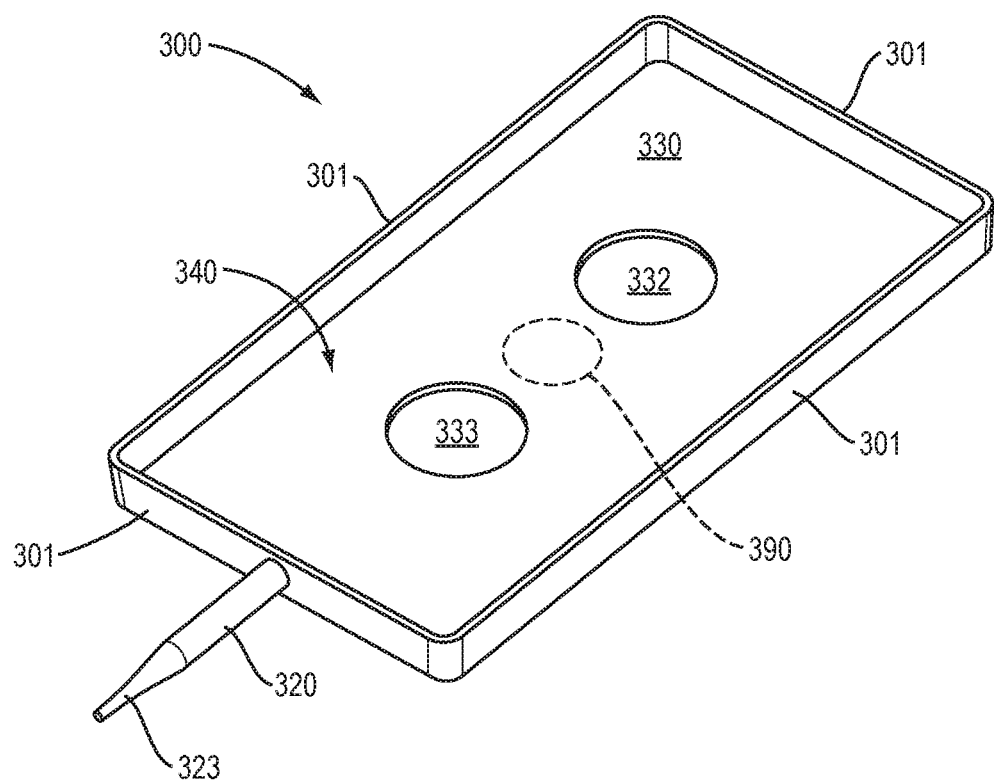
FIGS. 3, 4 and 5 show rigid structures that each include both ground and probe electrodes.
Figure 4:
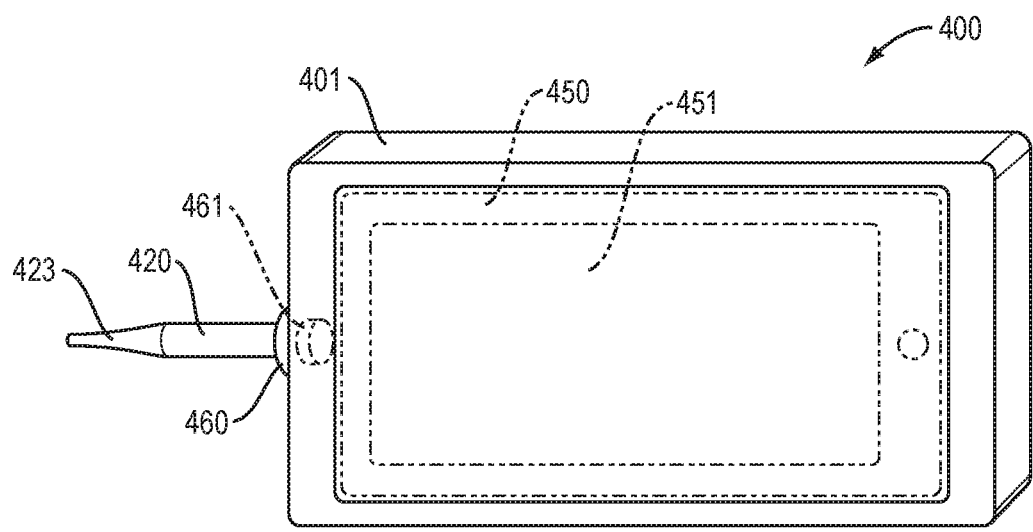
Figure 5:
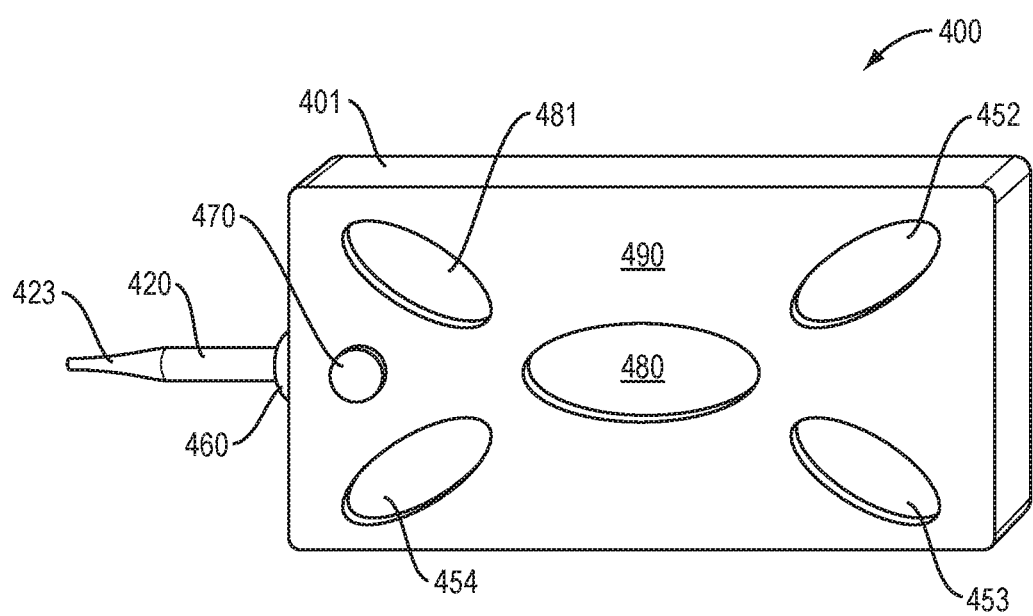

FIGS. 3, 4 and 5 show rigid structures that each: (a) are part of a current sensor; and (b) include both ground and probe electrodes.

In the example shown in FIG. 3, rigid structure 300 is configured to fit tightly around, and to hold in place, a smartphone. Put differently, rigid structure 300 may function in part as a rigid case that partially surrounds, and holds in place, a smartphone. Rigid structure 300 has a back 330 and walls 301. A smartphone may be inserted into a recessed region 340 of structure 300, in such a way that: (a) the smartphone presses against back 330 of structure 300; and (b) lateral movement of the smartphone is constrained by walls 301. Walls 301 may snap-fit around or press tightly against the smartphone, causing the smartphone to remain in recessed region 340 unless a user pulls on the smartphone to remove it from the recessed region. Back 330 has holes 332, 333, in order to reduce the weight of structure 300.

In FIG. 3, rigid structure 300 also includes a probe electrode 320 and a ground electrode 390. In FIG. 3, probe electrode 320 and a ground electrode 390 are rigid parts of a single rigid structure and thus are in a fixed position relative to each other. Probe electrode 320 includes a conductive tip 323. Ground electrode 390 (hidden from view in FIG. 3) and recessed region 340 are on opposite sides of back 330.

A patient: (a) may hold rigid structure 300 in one hand, in such a way that ground electrode is pressed against skin of the palm of that hand, and (b) may press the conductive tip 323 of probe electrode 322 against locations on the skin of other extremities. For instance, the patient may hold rigid structure 300 in the patient's left hand, while pressing tip 323 against a sequence of locations, such as six locations on the patient's right foot, then six locations on the patient's left foot, and then six locations on the patient's right forearm. The patient may then hold the rigid structure in the right hand, and press tip 323 against a sequence of six locations on the patient's left forearm. The current sensor may measure cross-body currents when the probe electrode is at each of these different locations.

FIGS. 4 and 5 show a front view and back view, respectively, of a rigid structure 400. Rigid structure 400 functions in part as a case for a smartphone. Walls 401 and back 490 form a recessed region into which a smartphone 450 may be inserted. Smartphone 450 may include touch screen 451.

In the example shown in FIGS. 4 and 5, rigid structure 400 includes a probe electrode 420 with a conductive tip 423, and also includes a ground electrode. This ground electrode has six conductive pads 452, 453, 454, 480, 481, 470. Again, a patient may hold rigid structure 400 in one hand, with ground electrode pressed against the skin of the palm of that hand, while pressing the probe electrode 420 against the skin at different locations on other extremities of the patient's body. The current sensor may measure cross-body currents at each of these measurement locations. An electronics module 460 may include an ADC, other signal processing circuitry and a microcontroller. Electronics module 460 may include an ammeter. The hardware and functionality of the ammeter in electronics module 460 may be the same as described above with respect to ammeter 122. An interface module 461 may include electronic components and other circuitry for interfacing with the smartphone. In some cases, interface module 461 is self-cleaning or self-polishing. For instance, interface module 461 may include pliant layers that tend to scrape debris off of conducting electrodes when the smartphone (or other mobile computing device) is being inserted into the recessed region of the rigid structure 400. These pliant layers may comprise Teflon®.

In some use scenarios, it is desirable to measure how forcefully the ground electrode and/or probe electrode are being pressed against skin of the patient. This is because the amount of pressure exerted by an electrode against the patient's skin may significantly affect the current measurements. For example, if a patient presses against the ground electrode much harder when the probe electrode is in a first position than when the probe electrode is in a second position, the extra pressure in the first position may, unless corrective measures are taken, cause current measurements at the two positions to be incomparable.

In some implementations, this problem (different amounts of pressure exerted by the user affects magnitude of current measurements) is mitigated by employing a pressure sensor that measures the amount of force or pressure exerted against a ground electrode or probe electrode. For instance, the ground electrode or probe electrode may include or be attached to a pressure sensor. For instance, each of the six conductive pads 452, 453, 454, 480, 481, 470 of the ground electrode in FIGS. 4 and 5 may include or be attached to a pressure sensor. Any type of pressure sensor may be employed. For example, the pressure sensor may comprise: (a) a piezoresistive strain gauge; (b) a capacitive strain gauge (e.g., a variable capacitor in which capacitance decreases as a diaphragm deforms due to increasing pressure); (c) an electromagnetic pressure sensor (e.g., that measures displacement of a diaphragm by changes in inductance, or by Hall Effect, or by eddy current); (d) an optical strain gauge (e.g., that employs fiber Bragg gratings); or (e) a potentiometric strain gauge (e.g., in which change of position of a conductive element causes a change in resistance). Each time that a cross-body current is measured, the pressure sensor may measure pressure (or force) exerted against the probe electrode or the ground electrode.

In some cases, the ground electrode and probe electrode are rigid parts that are part of a rigid single structure and that thus are in a fixed position relative to each other, except for any movement that occurs due to varying displacement within a pressure sensor due to varying pressure or force exerted against the pressure sensor.

Alternatively: (a) smartphone 450 may be replaced by any other mobile computing device; and (b) rigid structure 400 may be a case that surrounds, and holds in place, the mobile computing device. For instance, the mobile computing device may be a tablet computer, notebook computer, mobile internet device, personal digital assistant, handheld PC, or ultra-mobile PC.

Figure 6:
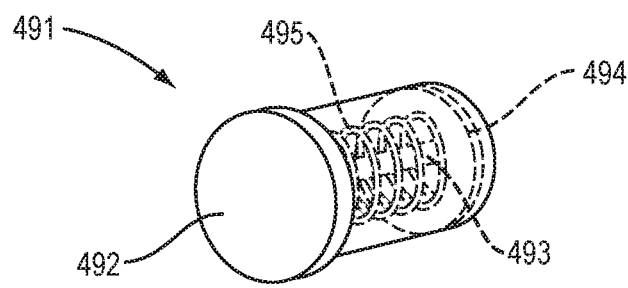
FIG. 6 shows a spring-loaded electrode.

FIG. 6 shows a closeup view of the spring-mounted pad 491, which is part of a ground electrode. This spring-mounted pad includes a conductive tip 492, a spring 495, a rod 493, and a pressure sensor 494. For instance, pressure sensor 494 may comprise a piezoelectric, inductive, potentiometric or optical pressure sensor. Rod 493 is physically attached to conductive tip 492. Pressure exerted against conductive tip 492 causes the tip 492 and rod 493 to be displaced. Specifically, tip 492 and rod 493 are constrained to move along a single axis in a limited range of motion. Varying displacement of rod 493 is measured, as a proxy for the pressure (or force) exerted against tip 492.

Each of six conductive pads 452, 453, 454, 480, 481, 470 of the ground electrode in FIGS. 4 and 5 may be spring-mounted, in the manner shown in FIG. 6.

In FIGS. 1, 2, 3, 4 and 5, one or both of the ground electrode and tip of the probe electrode may comprise a metallic alloy (e.g., copper/silver) that has antibacterial and antiviral properties. Alternatively, one or both of the ground electrode and tip of the probe electrode may comprise conductive rubber.

In some implementations, the ground electrode is temporarily attached to a patient's skin, rather than being held by a patient. For instance, the ground electrode may have an adhesive, conductive surface that adheres to the patient's skin. In some cases: (a) the ground electrode has multiple pads, and (b) each of the pads has a sticky, conductive surface that clings to the patient's skin.

In some alternative implementations, skin conductivity (or resistance) is measured instead of measuring current that flows through a patient's body between two electrodes. For instance, in some implementations, skin conductivity (or resistance) is measured by an infrared or optical sensor. In some cases, the sensor that measures skin conductivity (or resistance) does not contact the patient's skin. For example, a contact-less infrared or optical sensor may be employed to measure skin conductivity.

Measurement Locations

Before discussing measurement locations, let us first define "forearm" and "leg". As used herein, "forearm" means the portion of an upper limb of a human that is distal to the elbow. Thus, a forearm includes: (a) a hand; (b) a wrist; and (c) a region between elbow and wrist. As used herein, "leg" means the portion of a lower limb of a human that is distal to the knee. Thus, a leg includes a crus, an ankle and a foot.

As noted above, the current sensor may measure the cross-body electrical currents while the probe electrode is positioned at 24 locations on the skin of the patient's extremities, one location at a time. The measurement locations may consist of: (a) six locations on the right foot and six corresponding locations on the left foot; and (b) six locations on the right hand (or right wrist) and six corresponding locations on the left hand (or left wrist).

Figure 7:
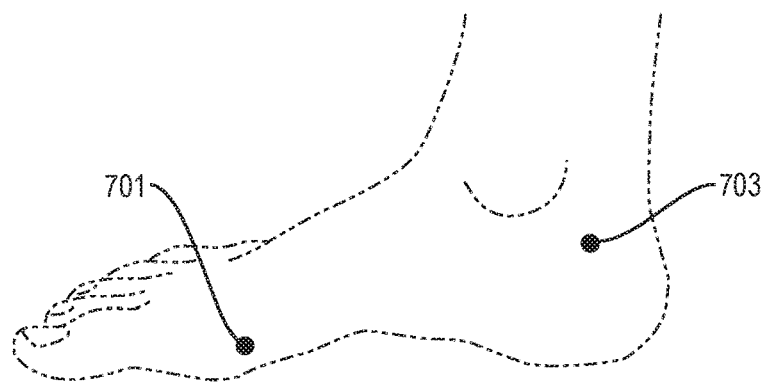
FIGS. 7, 8, 9, 10A and 10B show measurement points.
Figure 8:
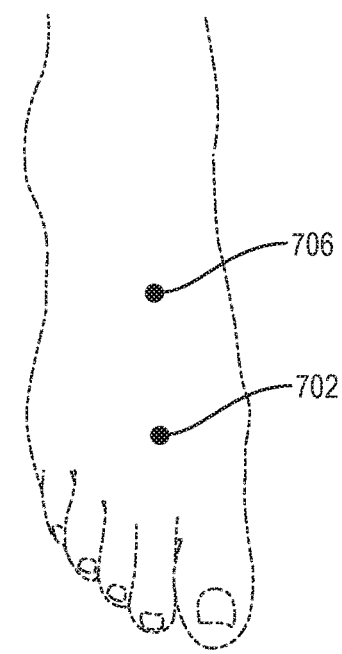
Figure 9:
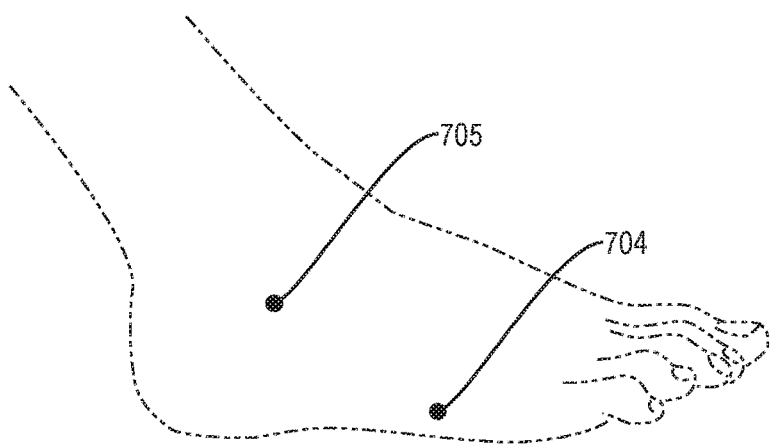

FIGS. 7, 8, and 9 show six locations 701, 702, 703, 704, 705, 706 on the right foot, at which the probe electrode may be placed (one location at a time) while the current sensor measures cross-body currents. These six locations on the right foot are positioned on acupuncture meridians. Specifically, locations 701, 702, 703, 704, 705, 706 are positioned on the Spleen, Liver, Kidney, Bladder, Gall Bladder, and Stomach acupuncture meridians, respectively. In acupuncture terminology: (a) location 701 is sometimes called SP3 or Spleen 3; (b) location 702 is sometimes called LR3 or Liver 3; (c) location 703 is sometimes called KI4 or Kidney 4; (d) location 704 is sometimes called BL65 or Bladder 65; (e) location 705 is sometimes called GB40 or Gall Bladder 40; and (f) location 706 is sometimes called ST42 or Stomach 42.

Likewise, the probe electrode may be placed (one location at a time) at six locations on the left foot, while the current sensor measures cross-body currents. These first, second, third, fourth, fifth and sixth locations on the left foot may be bilaterally symmetric with locations 701, 702, 703, 704, 705, and 706, respectively, on the right foot. Put differently, these first, second, third, fourth, fifth and sixth locations on the left foot of a patient may have reflectional symmetry (about the patient's sagittal plane) with locations 701, 702, 703, 704, 705, and 706, respectively, on the right foot of the patient. These six locations on the left foot may be positioned on the same acupuncture meridians—and have the same acupuncture meridian point numbers—as the respective corresponding locations on the right foot. For instance, the location on the left foot that is bilaterally symmetric with location 701 may be on the Spleen acupuncture meridian and may also be called SP3 or Spleen 3.

Figure 10A:
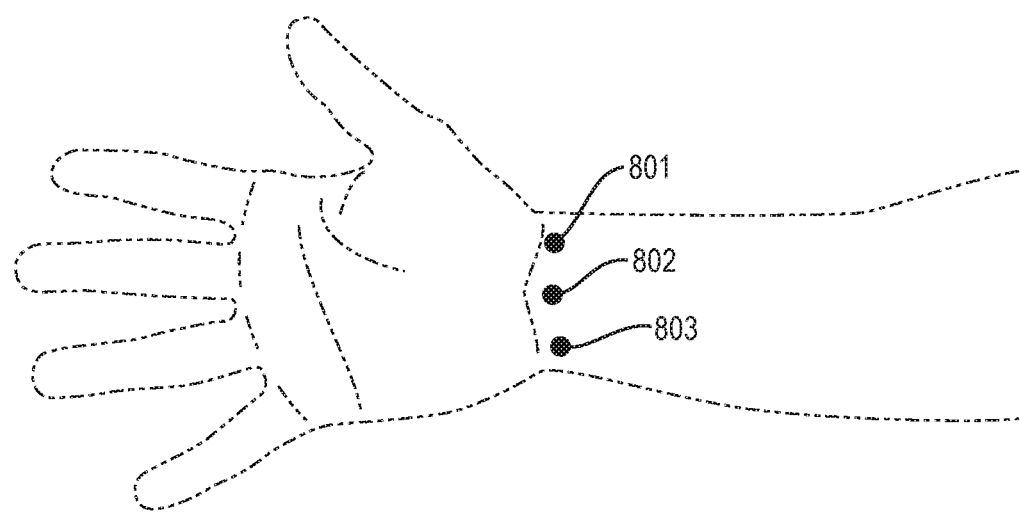
Figure 10B:
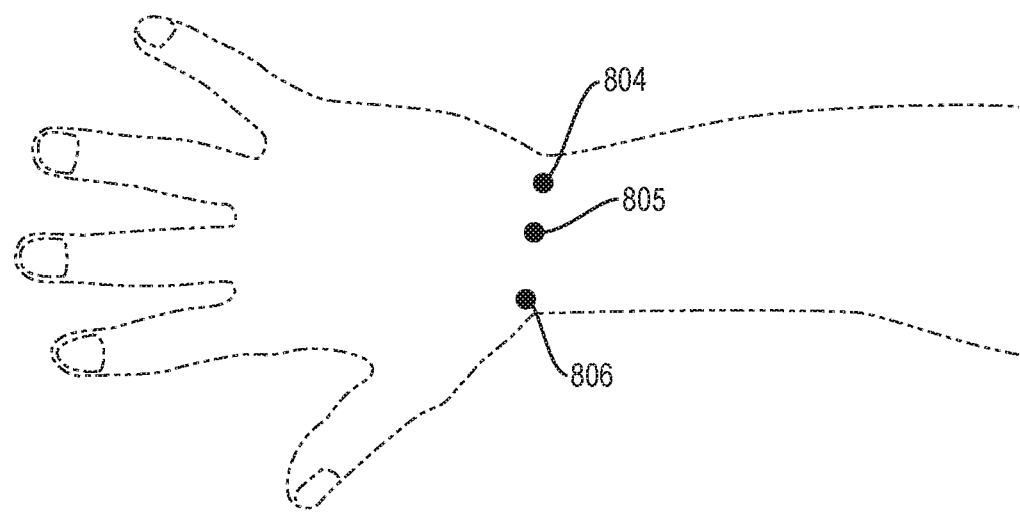

FIGS. 10A and 10B show six locations 801, 802, 803, 804, 805, 806 on the right forearm, at which the probe electrode may be placed (one location at a time) while the current sensor measures cross-body currents. These six locations on the right forearm are positioned on acupuncture meridians. Specifically, locations 801, 802, 803, 804, 805, 806 are positioned on the Lung, Pericardium, Heart, Small Intestine, Triple Heater and Large Intestine acupuncture meridians, respectively. In acupuncture terminology: (a) location 801 is sometimes called LU9 or Lung 9; (b) location 802 is sometimes called PC7 or Pericardium 7; (c) location 803 is sometimes called HT7 or Heart 7; (d) location 804 is sometimes called SI5 or Small Intestine 5; (e) location 805 is sometimes called TH4 or Triple Heater 4; and (f) location 806 is sometimes called LI5 or Large Intestine 5.

Likewise, the probe electrode may be placed (one location at a time) at six locations on the left forearm, while the current sensor measures cross-body currents. These first, second, third, fourth, fifth and sixth locations on the left forearm may be bilaterally symmetric with locations 801, 802, 803, 804, 805, and 806, respectively, on the right forearm. Put differently, these first, second, third, fourth, fifth and sixth locations on the left forearm of a patient may have reflectional symmetry (about the patient's sagittal plane) with locations 801, 802, 803, 804, 805, and 806, respectively, on the right forearm of the patient. These six locations on the left forearm may be positioned on the same acupuncture meridians—and have the same acupuncture point numbers—as the respective corresponding locations on the right forearm. For instance, the location on the left forearm that is bilaterally symmetric with location 801 may be on the Lung acupuncture meridian and may also be called LU or Lung 3.

As used herein, "Prototype Measurement Locations" means the 24 locations that are mentioned in the preceding four paragraphs (i.e., twelve locations 701, 702, 703, 704, 705, 706, 801, 802, 803, 804, 805, and 806 on the right side of a patient and twelve bilaterally symmetric locations on the left side of a patient).

Alternatively, the probe electrode may be placed at other acupuncture points. For each Prototype Measurement Location, another acupuncture point on the same meridian may be used instead. Put differently, rather than place the probe electrode at a Prototype Measurement Point on a given meridian, the probe electrode may instead be placed on another acupuncture point on the same meridian. For example, rather than place the probe electrode at a Prototype Measurement Point that is on a forearm and on a given meridian, the probe electrode may instead be placed on another acupuncture point that is on the same forearm and on the same meridian. Likewise, rather than place the probe electrode at a Prototype Measurement Point that is on a given meridian and is distal to a knee, the probe electrode may instead be placed on another acupuncture point that is on the same meridian and is distal to the same knee.

For instance: (a) to measure a cross-body electrical current for a Spleen meridian, the probe electrode may be placed at an acupuncture point that is on the Spleen meridian and is distal to a knee (e.g., at any of Spleen meridian points SP1 to SP8, inclusive); (b) to measure a cross-body electrical current for a Liver meridian, the probe electrode may be placed at an acupuncture point that is on the Liver meridian and is distal to a knee (e.g., at any of Liver meridian points LR1 to LR6, inclusive); (c) to measure a cross-body electrical current for a Kidney meridian, the probe electrode may be placed at an acupuncture point that is on the Kidney meridian and is distal to a knee (e.g., at any of Kidney meridian points KI 1 to KI 9, inclusive); (d) to measure a cross-body electrical current for a Bladder meridian, the probe electrode may be placed at an acupuncture point that is on the Bladder meridian and is distal to a knee (e.g., at any of Bladder meridian points BL55 to BL67, inclusive); (e) to measure a cross-body electrical current for a Gall Bladder meridian, the probe electrode may be placed at an acupuncture point that is on the Gall Bladder meridian and is distal to a knee (e.g., at any of Gall Bladder meridian points GB35 to GB44, inclusive); (f) to measure a cross-body electrical current for a Stomach meridian, the probe electrode may be placed at an acupuncture point that is on the Stomach meridian and is distal to a knee (e.g., at any of Stomach meridian points ST36 to ST45, inclusive); (g) to measure a cross-body electrical current for a Lung meridian, the probe electrode may be placed at an acupuncture point that is on the Lung meridian and is distal to an elbow (e.g., at any of Lung meridian points LU6 to LU11, inclusive); (h) to measure a cross-body electrical current for a Pericardium meridian, the probe electrode may be placed at an acupuncture point that is on the Pericardium meridian and is distal to an elbow (e.g., at any of Pericardium meridian points PC4 to PC9, inclusive); (i) to measure a cross-body electrical current for a Heart meridian, the probe electrode may be placed at an acupuncture point that is on the Heart meridian and is distal to an elbow (e.g., at any of Heart meridian points HT4 to HT9, inclusive); (j) to measure a cross-body electrical current for a Small Intestine meridian, the probe electrode may be placed at an acupuncture point that is on the Small Intestine meridian and is distal to an elbow (e.g., at any of Small Intestine meridian points SI 1 to SI 7, inclusive); (k) to measure a cross-body electrical current for a Triple Heater meridian, the probe electrode may be placed at an acupuncture point that is on the Triple Heater meridian and is distal to an elbow (e.g., at any of Triple Heater meridian points TH1 to TH9, inclusive); and (1) to measure a cross-body electrical current for a Large Intestine meridian, the probe electrode may be placed at an acupuncture point that is on the Large Intestine meridian and is distal to an elbow (e.g., at any of Large Intestine meridian points LI 1 to LI 9, inclusive).

Alternatively, in some implementations, less than 24 measurement locations are employed in a single diagnostic session. For instance, in some cases, the probe electrode is positioned (at different times during a single diagnostic session) at a total of 1, 2, 3, 4, 5, 6, 7, 8, 9, 10, 11 or 12 locations, while the current sensor measures cross-body electrical currents. In some cases: (a) the probe electrode is placed at 12 or less measurement locations during a single diagnostic session; and (b) half of the locations are on a right limb and half are on a left limb in bilaterally symmetric locations. In some cases, during a single diagnostic session, the probe electrode is placed at 12 or less measurement locations that are all on one or two forearms of the patient. For instance, in some cases, during a single diagnostic session, the probe electrode is placed at only 12 or less locations, all of which are on one or two wrists of the patient.

In some alternative implementations of this invention, the measurement locations are not on acupuncture points and are not located on acupuncture meridians. Put differently, when taking measurements of cross-body currents, the probe electrode may be pressed against the patient's skin at locations that are not acupuncture points and that are not on acupuncture meridians.

Currents

As used herein, a "Prototype Current" means an electrical current between a probe electrode and a ground electrode, which current is measured while: (a) the ground electrode is touching skin of a hand of a forearm of a patient; and (b) the probe electrode is touching skin of another limb of the patient at a Prototype Measurement Location.

As used herein, an "SP current" means an electric current between a probe electrode and a ground electrode, which current is measured while: (a) the ground electrode is touching skin of a hand of a patient; and (b) the probe electrode is touching skin of a leg of the patient at a location on the Spleen acupuncture meridian. As a non-limiting example, the location mentioned in the preceding sentence may be a Spleen 3 acupuncture point (e.g., location 701 on the patient's right leg in FIG. 7 or a bilaterally symmetric location on the patient's left leg).

As used herein, an "LR current" means an electric current between a probe electrode and a ground electrode, which current is measured while: (a) the ground electrode is touching skin of a hand of a patient; and (b) the probe electrode is touching skin of a leg of the patient at a location on the Liver acupuncture meridian. As a non-limiting example, the location mentioned in the preceding sentence may be a Liver 3 acupuncture point (e.g., location 702 on the patient's right leg in FIG. 8 or a bilaterally symmetric location on the patient's left leg).

As used herein, a "KI current" means an electric current between a probe electrode and a ground electrode, which current is measured while: (a) the ground electrode is touching skin of a hand of a patient; and (b) the probe electrode is touching skin of a leg of the patient at a location on the Kidney acupuncture meridian. As a non-limiting example, the location mentioned in the preceding sentence may be a Kidney 4 acupuncture point (e.g., location 703 on the patient's right leg in FIG. 7 or a bilaterally symmetric location on the patient's left leg).

As used herein, a "BL current" means an electric current between a probe electrode and a ground electrode, which current is measured while: (a) the ground electrode is touching skin of a hand of a patient; and (b) the probe electrode is touching skin of a leg of the patient at a location on the Bladder acupuncture meridian. As a non-limiting example, the location mentioned in the preceding sentence may be a Bladder 65 acupuncture point (e.g., location 704 on the patient's right leg in FIG. 9 or a bilaterally symmetric location on the patient's left leg).

As used herein, a "GB current" means an electric current between a probe electrode and a ground electrode, which current is measured while: (a) the ground electrode is touching skin of a hand of a patient; and (b) the probe electrode is touching skin of a leg of the patient at a location on the Gall Bladder acupuncture meridian. As a non-limiting example, the location mentioned in the preceding sentence may be a Gall Bladder 40 acupuncture point (e.g., location 705 on the patient's right leg in FIG. 9 or a bilaterally symmetric location on the patient's left leg).

As used herein, an "ST current" means an electric current between a probe electrode and a ground electrode, which current is measured while: (a) the ground electrode is touching skin of a hand of a patient; and (b) the probe electrode is touching skin of a leg of the patient at a location on the Stomach acupuncture meridian. As a non-limiting example, the location mentioned in the preceding sentence may be a Stomach 42 acupuncture point (e.g., location 706 on the patient's right leg in FIG. 8 or a bilaterally symmetric location on the patient's left leg).

As used herein, an "LU current" means an electric current between a probe electrode and a ground electrode, which current is measured while: (a) the ground electrode is touching skin of a hand of a forearm of a patient; and (b) the probe electrode is touching skin of the opposite forearm of the patient at a location on the Lung acupuncture meridian. As a non-limiting example, the location mentioned in the preceding sentence may be a Lung 9 acupuncture point (e.g., location 801 on the patient's right forearm in FIG. 10A or a bilaterally symmetric location on the patient's left forearm).

As used herein, a "PC current" means an electric current between a probe electrode and a ground electrode, which current is measured while: (a) the ground electrode is touching skin of a hand of a forearm of a patient; and (b) the probe electrode is touching skin of the opposite forearm of the patient at a location on the Pericardium acupuncture meridian. As a non-limiting example, the location mentioned in the preceding sentence may be a Pericardium 7 acupuncture point (e.g., location 802 on the patient's right forearm in FIG. 10A or a bilaterally symmetric location on the patient's left forearm).

As used herein, an "HT current" means an electric current between a probe electrode and a ground electrode, which current is measured while: (a) the ground electrode is touching skin of a hand of a forearm of a patient; and (b) the probe electrode is touching skin of the opposite forearm of the patient at a location on the Heart acupuncture meridian. As a non-limiting example, the location mentioned in the preceding sentence may be a Heart 7 acupuncture point (e.g., location 803 on the patient's right forearm in FIG. 10A or a bilaterally symmetric location on the patient's left forearm).

As used herein, an "SI current" means an electric current between a probe electrode and a ground electrode, which current is measured while: (a) the ground electrode is touching skin of a hand of a forearm of a patient; and (b) the probe electrode is touching skin of the opposite forearm of the patient at a location on the Small Intestine acupuncture meridian. As a non-limiting example, the location mentioned in the preceding sentence may be a Small Intestine 5 acupuncture point (e.g., location 804 on the patient's right forearm in FIG. 10B or a bilaterally symmetric location on the patient's left forearm).

As used herein, a "TH current" means an electric current between a probe electrode and a ground electrode, which current is measured while: (a) the ground electrode is touching skin of a hand of a forearm of a patient; and (b) the probe electrode is touching skin of the opposite forearm of the patient at a location on the Triple Heater acupuncture meridian. As a non-limiting example, the location mentioned in the preceding sentence may be a Triple Heater 4 acupuncture point (e.g., location 805 on the patient's right forearm in FIG. 10B or a bilaterally symmetric location on the patient's left forearm).

As used herein, an "LI current" means an electric current between a probe electrode and a ground electrode, which current is measured while: (a) the ground electrode is touching skin of a hand of a forearm of a patient; and (b) the probe electrode is touching skin of the opposite forearm of the patient at a location on the Large Intestine acupuncture meridian. As a non-limiting example, the location mentioned in the preceding sentence may be a Large Intestine 5 acupuncture point (e.g., location 806 on the patient's right forearm in FIG. 10B or a bilaterally symmetric location on the patient's left forearm).

As used herein: (a) "right side" of a patient means the portion of the patient's body to the right of the patient's sagittal plane; (b) "left side" of a patient means the portion of the patient's body to the left of the patient's sagittal plane; (c) a current "on the right side" means a current that is measured while the probe electrode is placed at a measurement location on a patient's right side; and (d) a current "on the left side" means a current that is measured while the probe electrode is placed at a measurement location on a patient's right side. To say that a current is in a specific current range "on both sides" means that the current is in the specific current range when measured while the probe electrode is positioned at a measurement location on the right side and also in the same current range when measured while the probe electrode is positioned at a bilaterally symmetric location on the left side.

Figure 11:
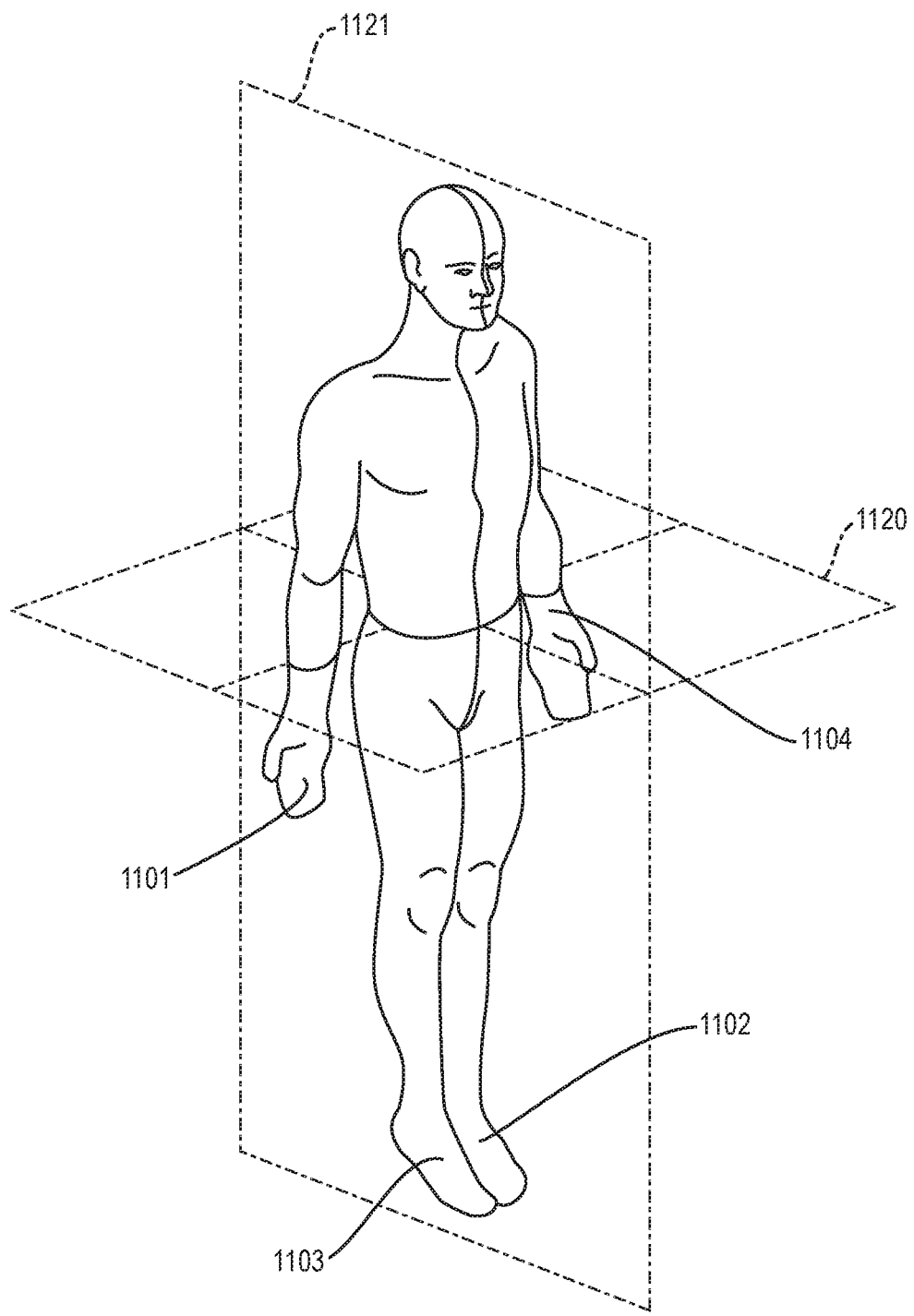
FIG. 11 illustrates cross-body currents.

FIG. 11 shows cross-body currents, in an illustrative implementation of this invention. In FIG. 11, sagittal plane 1121 divides a patient's body into right and left sides. Transverse plane 1120 intersects the patient's navel and divides the patient's body into upper and lower halves.

In FIG. 11, a first cross-body electric current flows between: (a) a probe electrode that touches the patient's left foot at location 1102; and (b) a ground electrode that touches the patient's right palm at location 1101. This first current passes through both sagittal plane 1121 and transverse plane 1120.

In FIG. 11, a second cross-body electric current flows between: (a) a probe electrode that touches the patient's right foot at location 1103; and (b) a ground electrode that touches the patient's right palm at location 1101. This second current passes through transverse plane 1120.

In FIG. 11, a third cross-body electric current flows between: (a) a probe electrode that touches the patient's left forearm at location 1104; and (b) a ground electrode that touches the patient's right palm at location 1101. This third current passes through sagittal plane 1121 and, depending on the positions of the user's hands, may also pass through transverse plane 1120.

Current Ranges

In some implementations, during a single diagnostic session, the current sensor (e.g., 122) takes multiple measurements of electrical current at each measurement location. Put differently, the current sensor may take multiple measurements of electrical current at each point on the patient's skin where the probe electrode is placed.

Each of these current measurements may be calibrated. For instance, the current measurements may be calibrated based on simultaneous pressure measurement(s) that is/are indicative of pressure or force exerted against the probe electrode or ground electrode. The calibration may eliminate the impact of varying pressure or force on the magnitude of the current readings.

The calibrated measurements for a single measurement location may be filtered to eliminate outliers.

Thus, for each single measurement location, multiple calibrated, filtered current measurements may be taken.

The measurements for a single measurement location may (after any calibration and/or filtering) be averaged, to yield an average value for that measurement location. For instance, the current sensor may take 20 measurements of SP current while: (a) the ground electrode is touching the same region of skin on a hand of a patient; and (b) the probe electrode is touching the patient's skin at location 701 on the patient's right leg. These 20 measurements of SP current may (after any calibration and/or filtering) be averaged, resulting in an average SP current.

This process of calculating an average current for each measurement location may be repeated for multiple measurement locations on a single patient during a single diagnostic session. In some cases: (a) current measurements are taken at 24 different measurement locations on a single patient during a single diagnostic session; and (g) 24 average currents are calculated, one for each of the 24 measurement locations.

The average values for the respective measurement locations for the diagnostic session may then be averaged, resulting in an overall average current for the patient for the diagnostic session. For instance, in some cases: (a) there are 24 measurement locations; and (b) the overall average current is an average of the 24 average currents for the respective 24 measurement locations.

A set of current ranges for the patient for the diagnostic session may then be calculated. In some cases, we call these current ranges: (a) "way above average"; (b) "above average"; (c) "average"; (d) "below average" and (e) "way below average". The amperage in the "way above average" range is greater than in the "above average" range, which in turn is greater than in the "average" range", which in turn is greater than in the "below average" range, which in turn is greater than in the "way below average range.

In some implementations: (a) the "average range" is selected in such a way as to be centered on the overall average current; and (b) the magnitude of the difference (in amperes) between the lower bound of the "way above average" range and the upper bound of the "average" range is equal to the magnitude of the difference (in amperes) between the lower bound of the "average" range and the upper bound of the "way below average" range.

In some implementations, one or more computers calculate, based on the overall average current for a patient for a diagnostic session, what we call Prototype Current Ranges for the patient for the diagnostic session.

As used herein, "Prototype Current Ranges" for a diagnostic session mean a set of current ranges in which: (a) the set consists of five current ranges, specifically, a "way above average" range, an "above average" range, an "average" range, a "below average" range, and a "way below average" range; (b) amperage in the way above average range is greater than amperage in the above average range, which in turn is greater than amperage in the average range, which in turn is greater than amperage in the below average range, which in turn is greater than amperage in the way below average range; (c) the upper bound of the average range is equal to the overall average current for the diagnostic session plus 25 microamps; (d) the lower bound of the average range is equal to the overall average current for the diagnostic session minus 25 microamps; (e) the upper bound of the above average range is equal to the overall average current for the diagnostic session plus 50 microamps; and (e) the lower bound of the below average range is equal to the overall average current minus 50 microamps. Notwithstanding the foregoing, a current range in the "Prototype Current Ranges" shall be truncated or eliminated to the extent needed to cause all values in the Prototype Current Ranges to be positive. For purposes of the definition of "Prototype Current Ranges" for a diagnostic session, the "overall average current" means an average of currents (after any calibration and/or filtering) for the respective measurement locations during the diagnostic session.

In illustrative implementations, a current for each measurement location is assigned to one of the calculated current ranges. For instance, in some cases: (a) current measurements are taken at 24 different measurement locations on a single patient during a single diagnostic session; (b) 24 currents are calculated, one for each of the 24 measurement locations; and (c) each of the 24 currents is assigned to one of the calculated current ranges. Each current that is assigned to a current range may itself be an average, calibrated and/or filtered current, as described above.

Alternatively, in some cases: (a) only a single current measurement is taken at each measurement location during a diagnostic session; (b) the overall average current is equal to the average of these single current measurement for the respective measurement locations; and (c) the single current measurements for the respective measurement locations are each assigned to a current range. In some cases, calibration and/or filtering are not performed, and the overall average current is calculated with uncalibrated and/or unfiltered data.

Lookup Table

In some implementations, after currents for the respective measurement locations are each assigned to a current range, a computer employs a look up table to determine one or more medical conditions that are indicated by one or more of these currents. For instance, the computer may determine whether one or more of these currents is or are in a specific state that is listed in the lookup table, and may further determine that this specific state is associated (by the look up table) with one or more specific medical conditions, and may thus conclude that the current readings in the diagnostic session indicate that these one or more specific medical conditions are present. Put differently, the computer may conclude that the specific state (of electrical currents) exists and is a biomarker for the one or more specific medical conditions.

For instance, a computer: (a) may determine that HT current and PC current are in a specific state, in which HT current is below average on the left, the right or both sides of a patient and the PC current is below average on the left, the right or both sides of the patient; (b) may access a lookup table and determine that this specific state is associated (by the lookup table) with coronary artery disease; and (b) may thus conclude that coronary artery disease is indicated by the current readings. Put differently, the computer may conclude that a specific current state (of HT and PC currents) exists and is a biomarker for coronary artery disease.

In some use scenarios, a single current state is associated (by the lookup table) with more than one medical conditions.

Each specific current state may consist of either: (a) a current range for a single current (e.g., SP current is below average on left and right sides); or (b) current ranges for multiple respective currents (e.g., GB current is way below average on left and right sides and LR current is average on left and right sides).

In some implementations, the lookup table is also employed to determine a confidence level or probability for a particular medical condition. For instance, the lookup table may associate a specific current state with both: (a) a medical condition; and (b) a confidence level or probability for that condition. The confidence level or probability may be explicit or implicit. For instance, the lookup table may indicate that a recommendation should be made for further medical testing, in order to evaluate whether or not a specific medical condition is actually present. We sometimes call this a "rule-out" recommendation.

In some implementations, the lookup table includes all or part of the information set forth in Table 1 below. For instance, the lookup table may include at least part of the information (about medical conditions, electric current states and associations between electrical current state and medical condition) which is set forth in Table 1 below.

TABLE 1

| | Class | Medical Condition | Electrical Current State |
|---|---|---|---|
| 1. | B | anemia | (a) SP current is below average on left and right sides; and<br>(b) KI current is average on left and right sides; and<br>(c) BL current is average on left and right sides. |
| 2. | A | anxiety | [(a) HT current is above average on left, right or both sides; and<br>(b) LR current is average on left and right sides]<br>and/or<br>[(a) LU current is average on left, right or both sides; and<br>(b) PC current is average on left, right or both sides; and<br>(c) HT current is average on left, right or both sides; and<br>(d) LR current is average on left and right sides.]<br>and/or<br>[(a) HT current is above average on left and right sides; and<br>(b) SI current is above average on left, right or both sides]. |
| 3. | D | back injury | BL current is above average on left, right or both sides. |
| 4. | D | back injury - with nerve damage and no pain | (a) BL current is below average on left, right or both sides; and<br>(b) SP current is below average on left, right or both sides. |
| 5. | D | back injury - with nerve damage and pain | (a) BL current is above average on left, right or both sides; and<br>(b) SP current is below average on left, right or both sides. |
| 6. | D | back injury - with pain | BL current is above average on left, right or both sides. |
| 7. | B | bacterial infection | (a) SP current is way above average on left and right sides; and<br>(b) KI current is average on left and right sides; and<br>(c) BL current is average on left and right sides. |
| 8. | A | bipolar disorder - in depressive state | (a) PC current is below average on left and right sides; and<br>(b) HT current is below average on left and right sides; and<br>(c) LR current is above average on left and right sides. |
| 9. | A | bipolar disorder - in manic state | (a) LU current is way above average on left and right sides; and<br>(b) PC current is way above average on left and right sides; and<br>(b) HT current is way above average on left and right sides; and<br>(c) LR current is way above average on left and right sides. |
| 10. | G | bladder dysfunction | (a) BL current is above average on left, right or both sides; and/or<br>(b) BL current is below average on left, right or both sides. |
| 11. | B | bladder infection | (a) KI current is way above average on left and right sides; and<br>(b) BL current is way above average on left and right sides; and<br>(c) SP current is way above average on left and right sides. |
| 12. | I | blood pressure medication overdose | (a) PC current is below average on left and right sides; and<br>(b) HT current is below average on left and right sides. |
| 13. | G | chronic fatigue and/or chronic sleep deficit | (a) HT current is below average on left, right or both sides; and<br>(b) PC current is below average on left, right or both sides. |
| 14. | B | chronic obstructive pulmonary disease | (a) LU current is above average on left and right sides; xor<br>(b) LU current is below average on left and right sides. |
| 15. | B | constipation | (a) LI current is below average on left, right or both sides; and<br>(b) SI current is average on left, right or both sides; and<br>(c) TH current is average on left, right or both sides. |
| 16. | M | coronaly artery disease | (a) HT current is below average on left, right or both sides; and<br>(b) PC current is below average on left, right or both sides. |
| 17. | J | deficiency in caloric food intake | (a) SI current is way below average on left and right sides; and<br>(b) TH current is way below average on left and right sides; and<br>(c) LI current is way below average on left and right sides; and<br>(d) ST current is way below average on left and right sides; and<br>(e) GB current is way below average on left and right sides. |
| 18. | J | deficiency in protein intake | LR current is below average on left and right sides. |
| 19. | I | mild (i.e., non-clinical) depression | (a) HT current is above average or below average on left side; and<br>(b) HT current is above average or below average on right side; and<br>(c) PC current is above average or below average on left side; and<br>(d) PC current is above average or below average on right side; and<br>(e) LR current is above average on left and right sides. |
| 20. | A | clinical depression | (a) PC current is below average on left, right or both sides; and<br>(b) HT current is below average on left, right or both sides; and<br>(c) LR current is above average on left, right or both sides; and<br>(d) ST current is average or below average on left, right or both sides. |
| 21. | K | poor glycemic control (if patient has diabetes mellitus) | SP current is below average on left and right sides. |
| 22. | I | digestive disorder | (a) LI current is average or below average on left side; and<br>(b) LI current is average or below average on right side; and<br>(c) ST current is way below average on left and right sides; and<br>(d) GB current is average on left and right sides. |

TABLE 1-continued

| | Class | Medical Condition | Electrical Current State |
|---|---|---|---|
| 23. | F | duodenal irritation | (a) SI current is above average on left, right or both sides; and (b) HT current is average on left and right sides) xor (HT current is below average on left and right sides)]; and (c) [(LR current is average on left and right sides) xor (LR current is below average on left and right sides)]; and (d) LI current is average on left and right sides. |
| 24. | L | dysautonomia | (a) PC current is way below average on left and right sides; and (b) HT current is way below average on left and right sides; and (c) SP current is way below average on left and right sides; and (d) KI current is way below average on left and right sides; and (e) BL current is way below average on left and right sides. |
| 25. | L | dysphagia | (a) [(PC current is above average on left and right sides) xor (PC current is way above average on left and right sides)]; and (b) GB current is above average on left and right sides. |
| 26. | J | excessive fat intake | (a) LR current is way above average on left and right sides; and (b) GB current is above average or way above average on left side; and (c) GB current is above average or way above average on right side; and (c) ST current is above average or way above average on left side; and (d) ST current is above average or way above average on right side. |
| 27. | I | fatigue | (a) PC current is below average on left, right or both sides; and (b) HT current is below average on left, right or both sides. |
| 28. | I | food-related sinus allergy | (a) LU current is below average on left, right or both sides; and (b) LR current is above average on left, right or both sides. |
| 29. | G | gallbladder disorder | (a) GB current is way below average on left and right sides; and (b) LR current is average on left and right sides. |
| 30. | M | gastroparesis | (a) ST current is way below average on left and right sides; and (b) GB current is average on left and right sides; and (c) SP current is way below average on left, right or both sides; and (d) KI current is way below average on left, right or both sides; and (e) BL current is way below average on left, right or both sides. |
| 31. | G | headaches | (a) PC current is below average on left, right or both sides; and (b) HT current is below average on left, right or both sides; and (c) [(KI current is above average on left, right or both sides) and/or (SP current is above average on left, right or both sides)]. |
| 32. | C | hypermetabolism | (a) SI current is way above average on left and right sides; and (b) TH current is way above average on left and right sides; and (c) LI current is way above average on left and right sides. |
| 33. | C | hypertension | (a) PC current is above average on left and right sides; and (b) [(HT current is above average on left and right sides) xor (HT current is way above average on left and right sides)]. |
| 34. | C | hyperthyroid | (a) TH current is above average on left and right sides; and (b) SI current is average on left and right sides; and (c) LI current is average on left and right sides. |
| 35. | C | hypotension | (a) [(PC current is below average on left and right sides) xor (PC current is way below average on left and right sides)]; and (b) [(HT current is below average on left and right sides) xor (HT current is way below average on left and right sides)]. |
| 36. | C | hypothyroid | (a) TH current is below average on left and right sides; and (b) SI current is average on left and right sides; and (c) LI current is average on left and right sides. |
| 37. | K | incontinence (if patent is female) | (BL current is below average on left, right or both sides) and/or (BL current is above average on left, right or both sides). |
| 38. | Q | inflammation | (a) LR current is way above average on left and right sides; and (b) GB current is average on left and right sides; and (c) ST current is average on left and right sides. |
| 39. | F | irritation of stomach lining | ST current is way above average on left, right or both sides. |
| 40. | E | irritation of nerves in both upper back and lower back | (a) BL current is above average on left, right or both sides; and (b) KI current is above average on left, right or both sides. |
| 41 | E | irritation of nerves in lower back | BL current is above average on left and right sides. |
| 42. | E | irritation of nerves in neck | KI current is above average on left, right or both sides. |
| 43. | M | kidney failure | (a) KI current is below average on left and right sides; and (b) BL current is below average on left and right sides. |
| 44. | I | large intestine disorder (with symptoms other than or in addition to large intestine irritation) | (a) LI current is below average on left, right or both sides; and/or (b) LI current is above average on left, right or both sides; and |

TABLE 1-continued

| | Class | Medical Condition | Electrical Current State |
|---|---|---|---|
| 45. | F | large intestine irritation | (a) LI current is way above average on left, right or both sides; and (b) SI current is average on left and right sides. |
| 46. | D | lower back injury | BL current is above average on left, right or both sides. |
| 47. | D | lower back pain | BL current is above average on left, right or both sides |
| 48. | Q | lung cancer | LU current is way above average on left, right or both sides. |
| 49. | Q | lung disease (excluding lung cancer) | (a) LU current is above average on left, right or both sides; and/or (b) LU current is below average on left, right or both sides |
| 50. | K | menstruating (if patient is a woman) | (a) SP current is above average on left and right sides; and (b) BL current is above average on left and right sides; and (c) KI current is above average on left and right sides. |
| 51. | Q | microcirculatory disease | PC current is below average on left, right or both sides. |
| 52. | N | microcirculatory-orthostatic hypotension | (a) PC current is below average on left and right sides; and (b) HT current is below average on left and right sides; and (c) SP current is below average on left and right sides; and (d) KI current is below average on left and right sides; and (e) BL current is below average on left and right sides. |
| 53. | N | multiple sclerosis | (a) KI current is below average on left and right sides; and (b) SP current is below average on left and right sides; and (c) BL current is below average on left and right sides. |
| 54. | H | nerve damage in lower back | BL current is below average on left, right or both sides. |
| 55. | H | nerve damage in neck | KI current is below average on left, right or both sides. |
| 56. | H | nerve damage due to fall on tailbone (in female patient) | (a) BL current is below average on left and right sides; and (b) KI current is average on left and right sides; and (c) SP current is average on left and right sides. |
| 57. | H | nerve damage in upper back | KI current is below average on left, right or both sides. |
| 58. | N | benign prostatic hyperplasia | (a) BL current is below average on left, right or both sides; and (b) KI current is average on left, right or both sides; and (c) SP current is average on left, right or both sides. |
| 59. | Q | prostate cancer | (a) BL current is above average on left, right or both sides; and (b) KI current is average on left and right sides; and (c) SP current is average on left and right sides. |
| 60. | P | reflux | (a) GB current is above average on left, right or both sides; and (b) ST current is above average on left, right or both sides. |
| 61. | P | sinus infection | (a) SP current is way above average on left and right sides; (b) KI current is average on left and right sides; and (c) BL current is average on left and right sides; and (d) LU current is way below average on left and right sides. |
| 62. | L | sleep disorder | (a) HT current is below average on left and right sides; and (b) PC current is below average on left and right sides. |
| 63. | I | impaired stomach motility | (a) ST current is way below average on left and right sides; and (b) GB current is average on left and right sides. |
| 64. | J | excessive stress | [(a) HT current is above average on left, right or both sides; and (b) PC current is above average on left, right or both sides; and (c) SI current is below average on left, right or both sides] and/or [(a) HT current is average on left, right or both sides; and (b) PC current is average on left, right or both sides; and (c) ((SI current is above average on left, right or both sides) and/or (SI current is way above average on left, right or both sides))] |
| 65. | P | viral infection | (a) SP current is way below average on left and right sides; and (b) KI current is average or way above average on left, right or both sides; and (c) BL current is average or way above average on left, right or both sides. |

Table 1 has 65 rows.

Table 1 lists 65 electrical current states, i.e., one electrical current state per row. As used herein, "Prototype Electrical Current State" means an electrical current state that is listed in a row of Table 1. For instance, the Prototype Electrical Current State listed in row 3 of Table 1 is "BL current is below average on left, right or both sides." Also, for instance, the Prototype Electrical Current State listed in row 4 of Table 1 is "(a) BL current is below average on left, right or both sides; and (b) SP current is below average on left, right or both sides."

Each current range listed in Table 1 is a Prototype Current Range. Specifically, each time that a current range "way above average", "above average", "average", "below average" or "way below average" is listed in Table 1, that current range is a Prototype Current Range. For instance, in row 3 of Table 1, "above average" is a Prototype Current Range. Also, for instance, in row 28 of Table 1, "below average" and "above average" are each a Prototype Current Range.

Table 1 lists 65 medical conditions; i.e., one medical condition per row. As used herein, "Prototype Medical Condition" means a medical condition listed in a row of Table 1. For instance, the Prototype Medical Conditions listed in rows 1, 2 and 65 of Table 1 are anemia, anxiety and viral infection, respectively.

In each row in Table 1, the electrical current state listed in that row indicates that the patient has the medical condition listed in that row. Put differently, in each row in Table 1, the electrical current state listed in that row is a biomarker for the medical condition listed in that row. Likewise, in each row in Table 1, the electrical current state listed in that row is a factor that, in a differential diagnosis, points toward (or weighs in favor of) concluding that the patient has at least the medical condition listed in that row.

Table 1 associates Prototype Medical Conditions with respective Prototype Electrical Current States. Specifically, Table 1 associates the Prototype Medical Condition listed in each row of Table 1 with the Prototype Electrical Current State listed in that row. As a non-limiting example, Table 1 associates the Prototype Medical Condition listed in row 48 of Table 1 (i.e., lung cancer) with the Prototype Electrical Current State listed in row 48 of Table 1 (i.e., "LU current is way above average on left, right or both sides".)

As used herein, when the first letter of the verb "Associate" is capitalized, then to "Associate" means to associate, by a lookup table, a Prototype Medical Condition listed in a row of Table 1 with the Prototype Electrical Current State listed in that row of Table 1. The term "Associate" does not require accessing Table 1 itself; instead "Associate" requires a lookup table to make the same association as is made in a row of Table 1. For instance, if a lookup table were to associate lung cancer with the Prototype Electrical Current State "LU current is way above average on left, right or both sides", then the lookup table would be Associating lung cancer with that Prototype Electrical Current State. (This is because row 48 of Table 1 makes that association). The definition of "Associate" in this paragraph does not create any implication regarding the meaning of the word "associate" when the first letter of the word is not capitalized.

In each row in Table 1, if the electrical current state for that row does not explicitly mention a specific current, then that specific current may be in any Prototype Current Range. For instance: (a) in row 1 of Table 1, only SP current, KI current and BL current are explicitly mentioned; and (b) in the electrical current state listed in row 1, other currents (e.g., LR, GB, ST, LU, PC, HT, SI, TH and LI currents) may be in any Prototype Current Range.

Each current that is on a particular side of a patient and that is listed in Table 1 may have a value derived from: (a) a single measurement at a particular measurement location (after any calibration) or (b) multiple measurements at the particular measurement location (after any calibration and filtering). If a current listed in Table 1 has a value that is derived from multiple measurements at a particular measurement location, then that value is an average of the multiple measurements (after any calibration and filtering).

In some use scenarios, each current listed in Table 1 is a Prototype Current that is measured when a probe electrode is touching a Prototype Measurement Location. Likewise, in some use scenarios: (a) each current that is on a specific side of a patient and that is listed in Table 1 is an electric current between a probe electrode and a ground electrode, which current is measured while: (a) the ground electrode is touching skin of a hand of a forearm of a patient; and (b) the probe electrode is touching skin of another limb of the patient at a Prototype Measurement Location on that specific side of the patient.

This invention may be employed to accurately detect and diagnose medical conditions. For instance, in some implementations of this invention: (a) the Prototype Currents listed in Table 1 are measured while the probe electrode is placed at the Prototype Measurement Locations; (b) the measured currents are assigned to Prototype Current Ranges; and (c) accurate diagnoses of medical conditions are made based on the respective associations (between electrical current states and medical conditions) that are set forth in Table 1.

In Table 1, each medical condition is assigned a class. Specifically, each medical condition listed in a row of Table 1 is classified as being in a particular class, which particular class is listed in that row. For instance, in row 1 of Table 1, the medical condition of anemia is classified as being in Class B.

As used herein: (a) "Class A Condition" means a medical condition that is, in Table 1, classified as being in Class A; (b) "Class B Condition" means a medical condition that is, in Table 1, classified as being in Class B; (c) "Class C Condition" means a medical condition that is, in Table 1, classified as being in Class C; (d) "Class D Condition" means a medical condition that is, in Table 1, classified as being in Class D; (e) "Class E Condition" means a medical condition that is, in Table 1, classified as being in Class E; (f) "Class F Condition" means a medical condition that is, in Table 1, classified as being in Class F; (g) "Class G Condition" means a medical condition that is, in Table 1, classified as being in Class G; (h) "Class H Condition" means a medical condition that is, in Table 1, classified as being in Class H; (i) "Class I Condition" means a medical condition that is, in Table 1, classified as being in Class I; (j) "Class J Condition" means a medical condition that is, in Table 1, classified as being in Class J; (k) "Class K Condition" means a medical condition that is, in Table 1, classified as being in Class K; (1) "Class L Condition" means a medical condition that is, in Table 1, classified as being in Class L; (m) "Class M Condition" means a medical condition that is, in Table 1, classified as being in Class M; (n) "Class N Condition" means a medical condition that is, in Table 1, classified as being in Class N; (p) "Class P Condition" means a medical condition that is, in Table 1, classified as being in Class P; and (q) "Class Q Condition" means a medical condition that is, in Table 1, classified as being in Class Q. The medical conditions listed in this paragraph are each an example of a Prototype Medical Condition.

As noted above, the diagnostic system may determine whether or not a patient has a viral infection and whether or not a patient has a bacterial infection, based on electrical current measurements that take only a few minutes. This ability to quickly and accurately detect and differentiate between viral and bacterial infections enables the diagnostic system to be used as a mass-scale, rapid screening tool in a viral or bacterial epidemic.

For instance, the medical conditions listed in rows 7 and 65 of Table 1 are bacterial infection and viral infection, respectively. Table 1 associates bacterial infection with the electric current state listed in row 7 of Table 1 and associates viral infection with the electric current state listed in row 65 of Table 1. For example, if the electrical current state listed in row 65 of Table 1 is detected, then the diagnostic system may output a diagnosis that the patient has a viral infection. Likewise, if the electrical current state listed in row 7 of Table 1 is detected, then the diagnostic system may output a diagnosis that the patient has a bacterial infection.

Machine Learning

In some implementations of this invention, a computer employs a trained machine learning model instead of a lookup table, in order to predict a medical condition based on measurements of cross-body electrical currents.

In some implementations, the input to the machine learning model is data representing measurements of cross-body currents at multiple different measurement locations for a single patient during a single diagnostic session. For instance, the input to the machine learning model may comprise measurements of electrical currents, where: (a) the currents flow between a probe electrode and a ground electrode; and (b) the measurements are taken during a single diagnostic session while the patient holds the ground electrode and while the probe electrode is pressed against the patient's skin at each of multiple different locations on limbs of the patient, one location at a time.

In some cases, the data is calibrated (e.g., to adjust for the effect, if any, of pressure exerted against an electrode) and filtered (e.g., to remove outliers) before being fed as input into the machine learning model. In some cases: (a) multiple current measurements are taken at each measurement location; (b) the multiple measurements for each given location are averaged and the resulting average current for that given location is fed as an input into the machine learning model. In some cases: (a) the currents for the respective measurement locations are assigned into current ranges; and (b) the current ranges for the respective measurement locations are fed as inputs into the machine learning model. In some cases, one or more other features are extracted from the current measurements (and/or from contextual information), and are also fed as input into the machine learning algorithm.

In some implementations, the machine learning model that is used to predict medical conditions is a supervised learning algorithm, such as a decision tree algorithm, random forests algorithm, ANN (artificial neural network), CNN (convolutional neural network), RNN (recurrent neural network), RNN with LSTM (long short term memory), RNN with Gated Recurrent Unit, MLP (multi-layered perceptron), or SVM (support vector machine) algorithm or a classifier such as a KNN (k-nearest neighbors) or naive Bayes algorithm. The supervised learning model may be trained on a training dataset that has been labeled by a health care worker or other human expert. The labels may be medical conditions. The data that is labeled may comprise electrical current measurements or data or features derived therefrom. In some cases: (a) there are practical difficulties in obtaining a sufficiently large dataset for training; and (b) a generative model (e.g., a variable autoencoder or generative adversarial network) is employed to generate a synthetic database. This synthetic database may be added to a database derived from actual measurements, in order to form a large training database for supervised learning.

In some other implementations of this invention, the machine learning model that is used to predict medical conditions is a reinforcement learning algorithm (such as a Monte Carlo, Q-learning, state-action-reward-state-action, or deep Q network algorithm). Alternatively, the machine learning model that is used to predict medical conditions is an unsupervised machine learning algorithm, such as an AE (auto-encoder), SAE (stacked auto-encoder) VAE (variational auto-encoder), DBN (deep belief network), GAN (generative adversarial network), conditional GAN, or info-GAN algorithm. Or, for instance, the machine learning model may comprise a restricted Boltzmann machine.

In some implementations, the machine learning model outputs both: (a) one or more predicted medical conditions; and (b) a confidence level or probability for each of the one or more predicted medical conditions. Again, the confidence level or probability may be explicitly stated or may be implicit. For instance, the machine learning model may output a list of medical conditions, ranked from most probable to less probable. Or, for instance, the machine learning algorithm may output a "rule-out" recommendation—that is, a recommendation that further medical tests be performed to evaluate whether or not a specific medical condition is actually present.

In some implementations: (a) the machine learning model is a supervised learning algorithm; (b) after the model is initially trained, additional data is gathered based on ongoing experiences with patients; and (c) this additional data is labeled and used for additional training of the machine learning model.

User Interface

In some implementations, one or more computers control input/output (I/O) devices in such a way as to present a GUI (graphical user interface) or audiovisual UI (user interface) to a patient, health care worker or other user. For instance, a touch screen or other electronic display screen (e.g., 133, 451) may render a GUI. The patient, health care worker or other user may interact with the GUI by inputting instructions or data via one or more I/O devices such as a touch screen, keyboard 134, or mouse 135. In some implementations, the I/O devices present an audiovisual UI, including audio information outputted by speaker 132. In this audiovisual UI, audio input by the user may be detected by microphone 131 or by a microphone onboard smartphone 450.

The GUI or UI may present (to a patient, health care worker or other user) information about, among other things: (a) electrical current measurements taken during a diagnostic session; (b) current ranges assigned to different currents; (c) a diagnosis or tentative diagnosis that specifies one or more medical conditions that are indicated by the electrical current measurements taken during the diagnostic session; (d) a confidence level or probability associated with each diagnosis or tentative diagnosis; (e) one or more recommendations for action to be taken (e.g., a recommendation to check with a physician for further testing or for confirmation or treatment of a medical condition); (f) additional information about the diagnostic process and the current measurements; (g) results of previous diagnostic sessions; and (h) a comparison of a current diagnosis (or diagnoses) with a past diagnosis (or diagnoses).

The GUI or UI may include a chat box. The chat box may enable a patient to provide additional information about symptoms and to ask questions. In some cases, the chatbox will enable a patient to select from a list of symptoms, and also enable the patient to input information about symptoms that are not listed. The chat box may also enable a health care worker to ask additional questions and to receive answers from the patient.

One or more computers may employ a chatbot in a UI, in order to gather input from and provide information to a patient, health care worker or other user. In some cases, at least some of the information that is provided to a patient, health care worker or other user is sent via one or more emails or other social media messages. The information that is provided by chatbot, email or other social media message may comprise any or all of the information described above in this "User Interface" section.

In some cases, an audiovisual UI guides a user (e.g., patient or health care worker) to take the electrical current measurements under conditions that are suitable for accurate readings. Put differently, the audiovisual UI may provide real-time feedback regarding whether the electrodes are properly positioned and pressed firmly enough against the skin.

When an electrode is pressed against a patient's skin, the measured electrical current may increase as the pressure exerted against the skin increases, until the measured electrical current reaches a plateau. In some cases: (a) the current sensor detects when the electric current is increasing and when the current plateaus; (b) the only measurements of electric current that are used for diagnostic purposes occur after the measured current has increased and reached a plateau, and (c) measurements of electric current that are taken before the current reaches a plateau are disregarded for diagnostic purposes. Alternatively or in addition, in some cases: (a) one or more pressure sensors measure pressure exerted against an electrode; (b) the only measurements of electric current that are used for diagnostic purposes occur when the pressure exerted on the electrode exceeds a threshold value; and (c) measurements of electric current that are taken when the pressure exerted on the electrode is less than or equal to the threshold are disregarded for diagnostic purposes. In some cases, an electrode has multiple pads, and electric current measurements are disregarded for diagnostic purposes unless the pressure exerted against a threshold number of the pads exceeds a threshold pressure. In some cases, pressure is measured for both the ground electrode and probe electrode, and electric current measurements are disregarded for diagnostic purposes unless pressure exerted against each electrode exceeds the threshold pressure for that electrode. In some cases, the same pressure threshold is used for both the ground and probe electrodes and for all of the pads of a ground electrode. Alternatively, different pressure thresholds may be employed for different electrodes and/or for different pads of an electrode.

The audiovisual UI may emit a sound (e.g., a beep or tone) when the probe and ground electrodes are held correctly. The UI may include a sonic guide that changes pitch or tone depending on the amount of pressure applied to electrode(s) or depending on the amount of current being detected. The UI may also include a visual indicator that shows whether each electrode is in proper contact with the patient's skin. For instance, the graphic display may highlight which electrode is not properly contacting the patient's skin, by changing the color or shape of an electrode icon on the screen.

Thus, the UI may enable self-calibrated measurements of cross-body electrical currents on patients of varying measurement location physiologies (e.g., sizes, skin thickness, exact probe placement, variations in galvanic skin response and transient surface currents effects) and may be used to rapidly screen for optimal measurement protocols. In some implementations, the measurement protocol includes both: (a) real-time determination of quality of signal; and (b) real-time feedback to a user via the audiovisual UI.

Customization

In some cases, the machine learning algorithm is trained on a dataset for a general population.

In other cases, the machine learning algorithm is trained to predict medical conditions in a way that is customized for one or more features of a patient, such as the patient's age, sex, race, weight, habits (e.g., smoker vs non-smoker), personal medical history and/or family medical history. For instance, the training dataset for the machine learning algorithm may be labeled with not only medical conditions but also with one or more these features (e.g., patient's age, sex, race, weight, habits, personal medical history and/or family medical history).

Likewise, if a lookup table is employed instead of a machine learning algorithm, then multiple lookup tables may be used, each customized for a different combination of these features. As a non-limiting example, there may be a first lookup table for males over age 59, a second lookup table for women over age 59, a third lookup table for males age 31-59, and so on.

In some implementations of this invention, a machine learning model is personalized for a particular patient. For instance, a machine learning algorithm may be initially trained on data for a general population or for a subset of a general population. Then the machine learning algorithm may be further trained for a particular patient, based on data gathered in the course of performing diagnoses of the particular patient. For instance, if the machine learning algorithm predicts medical condition A for a patient but the patient actually has medical condition B, then this information may be used as part of an additional training dataset to train the machine learning algorithm to make personalized predictions for the patient.

Likewise, if a lookup table is employed instead of a machine learning algorithm, then the lookup table may be personalized, based on data gathered in the course of making diagnoses of the particular patient.

Adaptive Prediction

In some cases, the electrical current measurements for a patient are supplemented with information about contextual features. For instance, the contextual information may include sensor readings that are taken by one or more sensors which are worn by, or located near to, the patient. These other sensors may measure one or more physiological states of the patient (e.g., heart rate, respiration rate, body temperature) and/or one or more states of the patient's environment (e.g., temperature, humidity, ambient light). These other sensors may wirelessly transmit their readings to a receiver in the diagnostic system. In some cases, the contextual information also includes text or audio input from a patient or health care worker regarding the patient's state (e.g., happy, worried) and/or the patient's environment (e.g., at work).

In some cases, the machine learning algorithm is trained to adapt its prediction in real time based on data about the patient's context. For instance, the training dataset for the machine learning algorithm may be labeled with not only medical conditions but also with one or more contextual features (such as one or more physiological states, mental states, and environmental features). Likewise, if a lookup table is employed, different versions of the lookup table may be employed, depending on the patient's context.

After a machine learning model is initially trained, it may adaptively learn based on the patient's context when electric current measurements are taken. Data regarding both the electrical currents and the context may be gathered while making diagnoses and may later be employed as an additional training dataset, in order to further train the model to predict medical conditions in a manner that depends in part on context.

Machine Learning Example

The following 23 paragraphs describe an example (the "ML Example") of a diagnostic system that employs a trained machine learning model. The ML Example is a non-limiting example of this invention.

In this ML Example, a diagnostic system captures, organizes and analyzes measurements of electrical currents. The system employs machine learning and a database (knowledge library). The system may be used by less experienced practitioners to quickly and accurately diagnose their patients.

In this ML Example: (a) electrical current (or conductivity of the skin) is measured at each meridian point; and (b) excessive and deficient energies are plotted on a chart and identified. Treatment may consist of stimulating specific acupuncture points to either "tonify" a deficient meridian, or "sedate" an excessive meridian.

In this ML Example, patients have different electrical conductivity potentials. Thus, in this ML Example, current measurements are not absolute, but rather may be taken relative to all other measurements on the same patient. Thus, deviation from an average measurement may be more important than the actual measurement itself. Deviations (which may be used for diagnosis) may be determined by analyzing measurements within a broader context (e.g., plotting the current measurements on a chart and looking for outliers from the mean). For instance, an analysis may be designed to encompass the majority of measurements, in an area we sometimes call a "physiological corridor." Measurements outside the corridor may be deemed abnormal, and treatment applied to restore balance to abnormal meridians.

In this ML example, screening may be employed to identify the possible presence of an as-yet-undiagnosed disease in an individual patient (e.g., without signs or symptoms). This may include individuals with pre-symptomatic or unrecognized symptomatic disease.

In this ML Example, electrical measurements along acupuncture meridian lines may be used to examine and identify an individual's specific areas of weakness and strength in order determine a condition, disease or illness. The electrical conductance of the primary meridian lines may be measured at various points on the patient's wrists and ankles. Both excessive and deficient electrical conductance levels outside the patient's normal range may be correlated to classify the condition of the patient.

In this ML Example, a differential diagnostic process may distinguish a particular condition from others that present similar symptoms. A differential diagnosis may include the following steps: (a) gather information about the patient to be diagnosed and create a symptoms list; (b) list possible causes (candidate conditions) for the symptoms; (c) prioritize the list by placing the most urgently dangerous condition at the top of the list; (d) work down the list to rule out possible causes; and (e) remove diagnoses from the list by observing and applying tests that produce different results.

In this ML Example, meridian point assessment of the patient's condition may be used to assemble and support possible candidate conditions and also potentially rule out other possible causes from consideration.

In this ML Example, the diagnostic system may be applied to assess the mental health status of a patient.

In this ML Example, the mental health or psychiatric condition of the patient's mind may have adverse effects on the patient's body. For example, anxiety or depression (rather than an infection or physical abnormality in the digestive tract) may be the root cause of dyspepsia. The conductivity measurements may also provide data regarding psychological aspects of an individual, not just the physical.

In this ML Example, the diagnostic system may be a decision/support system that: (a) links observations with a database of knowledge; and (b) helps to analyze the current state of a patient and to reach a diagnostic conclusion.

Figure 12:
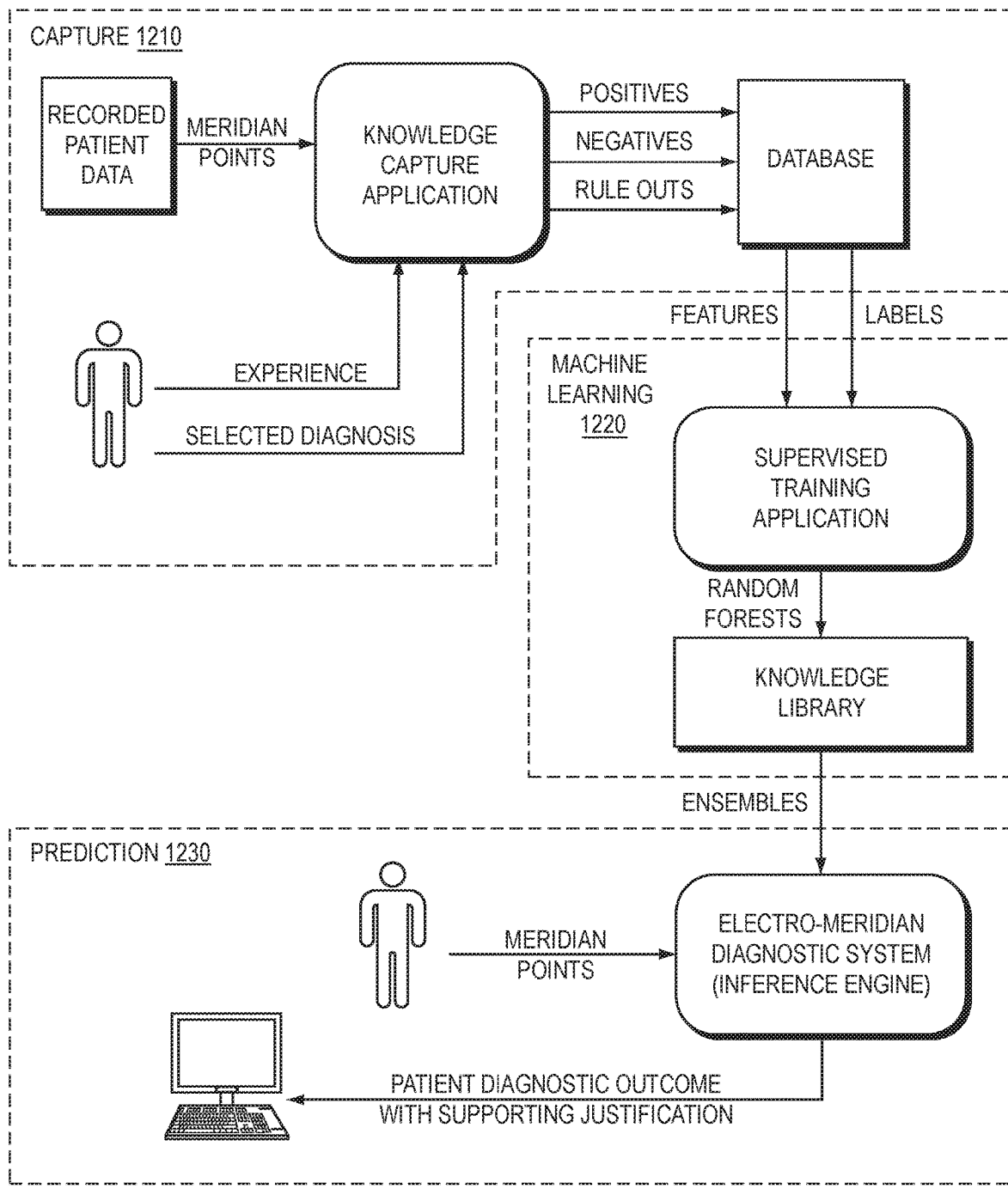
FIG. 12 is a flowchart for a diagnostic method.

FIG. 12 is a flowchart for a diagnostic method employed in the ML Example. The method shown in FIG. 12 includes at least the following steps: capture 1210, machine learning 1220, and prediction 1230.

In the ML Example, the capture step may comprise: (a) taking patient observations in the form of recorded meridian points; and (b) producing a database of associated labeled outcomes for a selected diagnosis (e.g., where the outcome labels are Positive, Negative and Rule Out). The information acquired during capture may be used to create the knowledge library database. Each patient record may consist of 24 meridian points, 12 from the left and right hands and 12 from the left and right feet.

In the ML Example, the machine learning step may include generating a set of random forests through supervised training, in such a way that: (a) one random forest is created for each potential diagnostic entity; and (b) the collection of random forests constitutes the knowledge library database.

In the ML Example, each random forest may be employed as an ensemble of knowledge for a given diagnostic conclusion. The conclusion may be either positive, negative or needs further testing to rule out. Each trained ensemble may represent a single hypothesis.

In the ML Example, any type of machine learning model may be employed, including: (a) an artificial neural network; (b) decision tree; (c) random forests; or (d) support vector machine.

In the ML Example, the machine learning model is trained by supervised learning. For example, the experience (and/or separate diagnosis) data entered by a doctor may be organized into the content of the models. Thus, a doctor may supervise the learning of the machine learning model.

In the version of the ML Example that is shown in FIG. 12, a doctor may enter a set of outcomes (positive, negative and/or rule out) for a specific set of patient meridian points as it relates to a specific diagnosis. Each experience is recorded in the database. In the supervised learning, the patient meridian points may be features and the outcomes may be labels. During supervised learning, a decision tree may split data into smaller data groups based on the features of the data until a small enough set of data identifies to one label. After the decision tree is trained, it may take as an input a feature set (meridian points) and may output one label (positive, negative or rule out).

In the ML Example, rather than rely on only one decision tree, a random forest is created that consists of a number of competing decision trees, where each tree is trained in a slightly different way. Then each tree in the forest may determine an answer on its own and the forest may be surveyed for the best agreed upon answer In the ML Example, the supervised learning mode may output an accurate predicted label (outcome). Meridian points recorded from a new patient may be entered into the diagnostic system and a patient diagnosis may be displayed on a practitioner's monitor.

In the ML Example, the machine learning algorithm may create a random forest for each diagnostic candidate and each forest may consist of hundreds of trees. As a non-limiting example, if there are a hundred diagnostic candidates, then there may be tens of thousands of decision trees that are making decisions (e.g., correlating meridian point data to possible outcomes).

In the ML Example, an inference engine may query each random forest for its outcome decision. The inference engine may assess the reliability of each decision, rank them and present them. The inference engine may also present supporting justification for the final set of outcomes. The inference engine may also record feedback from the practitioner to determine the validity of the final outcome. The information may be recorded and ultimately fed back into the machine learning algorithm to enhance system performance and accuracy.

Figure 13:
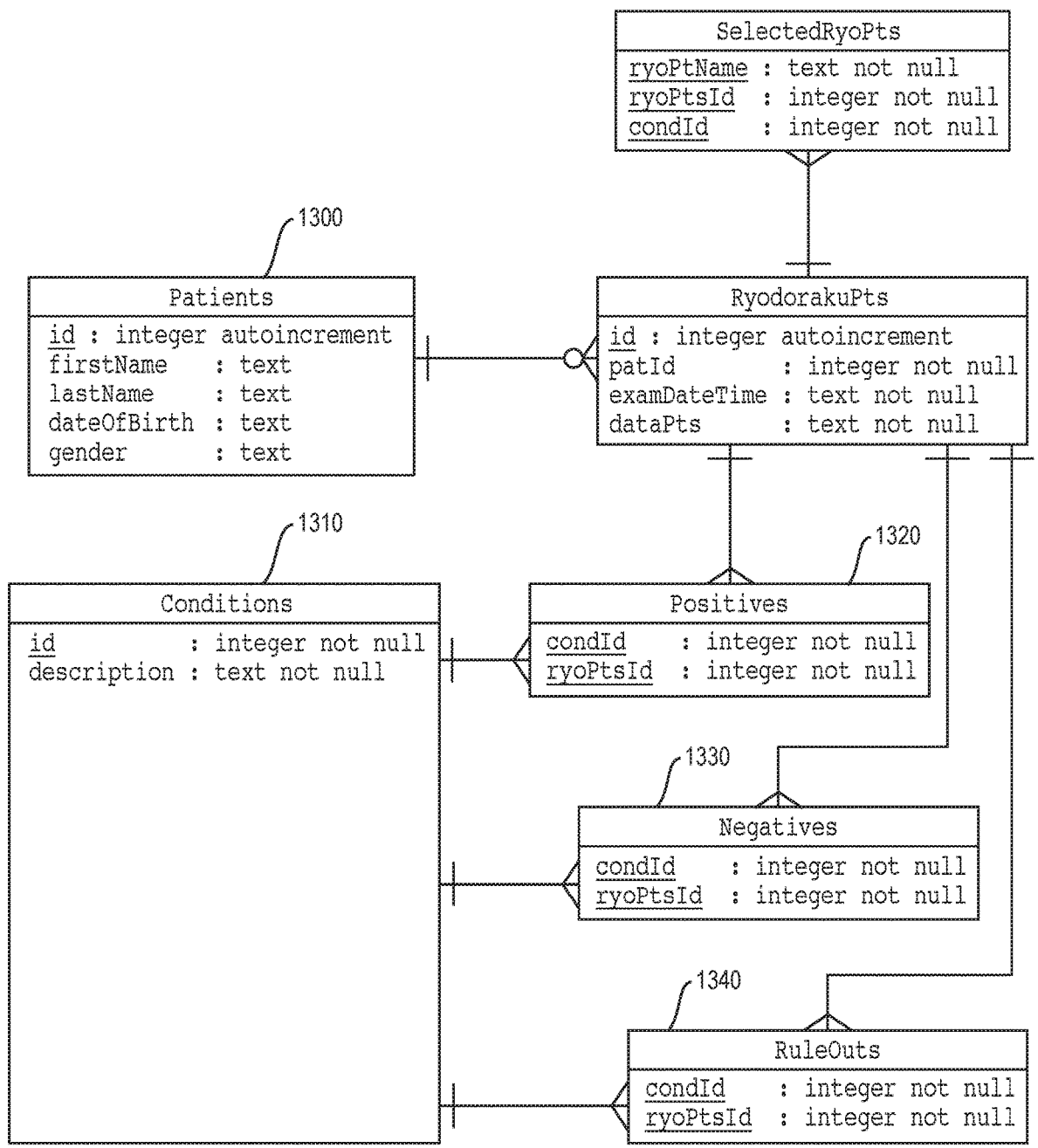
FIG. 13 is a diagram that illustrates a relational database.

In the ML Example, data may be stored in a relational database. For instance, data may be stored in the relational database shown in FIG. 13. This relational database may include data regarding, among other things, patients 1300, conditions 1310, positive outcomes 1320, negative outcomes 1330, and rule-outs 1340.

In the ML Example, each meridian record may be analyzed against the various diagnostic candidates and an outcome of positive, negative or rule out may be determined. A graphical user interface may display diagnostic results and may also display a justification for the diagnosis.

The ML Example described in the preceding 23 paragraphs is a non-limiting example of this invention. This invention may be implemented in many other ways.

Practical Applications

This invention has many practical applications. For instance, in some cases, the diagnostic system may be employed to diagnose or tentatively diagnose a medical condition. The diagnostic system may also be employed to screen for medical conditions, and to determine when further testing is needed in order to determine whether a particular medical condition is present. In some implementations, the diagnostic system is employed to quickly distinguish between a viral infection and a bacterial infection. Also, in some cases, the diagnostic system may be employed to rapidly screen for: (a) optimal dosing levels for medicine; (b) effects of (physical or psycho-) therapy or exercise; (c) effects of diet or other therapeutic or preventative or wellness-focused supplements; and (d) effects of pharmaceuticals and/or other therapeutic and diagnostic interventions.

Computers

In illustrative implementations of this invention, one or more computers (e.g., servers, network hosts, client computers, integrated circuits, microcontrollers, controllers, microprocessors, field-programmable-gate arrays, personal computers, digital computers, driver circuits, or analog computers) are programmed or specially adapted to perform one or more of the following tasks: (1) to control the operation of, or interface with, hardware components of a current sensor, power source, or signal generator; (2) to calibrate, filter and/or average current measurements; (3) to calculate current ranges and to assign currents to current ranges; (4) to determine an electrical current state that consists of a current range for a specific current or of current ranges for respective currents; (5) to access a lookup table to determine that one or more medical conditions are indicated by the electrical current state; (6) to train a machine learning model; (7) to employ a trained machine learning model to predict, based on measured cross-body electrical currents, that one or more medical conditions are present; (8) to output a diagnosis or tentative diagnosis; (9) to output a rule-out recommendation to perform further medical testing to evaluate whether a medical condition is actually present; (10) to output a probability or confidence level for each medical condition that is diagnosed or tentatively diagnosed; (11) to control input/output devices in such as to present a UI that provides real-time feedback regarding whether electrodes are being used properly and that provides other information including current readings and diagnoses; (12) to receive data from, control, or interface with one or more sensors, including one or more pressure sensors; (13) to perform any other calculation, computation, program, algorithm, or computer function described or implied herein; (14) to receive signals indicative of human input; (15) to output signals for controlling transducers for outputting information in human perceivable format; (16) to process data, to perform computations, and to execute any algorithm or software; and (17) to control the read or write of data to and from memory devices (tasks 1-17 of this sentence being referred to herein as the "Computer Tasks"). The one or more computers (e.g. 105, 121 or a computer in smartphone 450) may, in some cases, communicate with each other or with other devices: (a) wirelessly, (b) by wired connection, (c) by fiber-optic link, or (d) by a combination of wired, wireless or fiber optic links.

In exemplary implementations, one or more computers are programmed to perform any and all calculations, computations, programs, algorithms, computer functions and computer tasks described or implied herein. For example, in some cases: (a) a machine-accessible medium has instructions encoded thereon that specify steps in a software program; and (b) the computer accesses the instructions encoded on the machine-accessible medium, in order to determine steps to execute in the program. In exemplary implementations, the machine-accessible medium may comprise a tangible non-transitory medium. In some cases, the machine-accessible medium comprises (a) a memory unit or (b) an auxiliary memory storage device. For example, in some cases, a control unit in a computer fetches the instructions from memory.

In illustrative implementations, one or more computers execute programs according to instructions encoded in one or more tangible, non-transitory computer-readable media. For example, in some cases, these instructions comprise instructions for a computer to perform any calculation, computation, program, algorithm, or computer function described or implied herein. For instance, in some cases, instructions encoded in a tangible, non-transitory, computer-accessible medium comprise instructions for a computer to perform the Computer Tasks.

Computer Readable Media

In some implementations, this invention comprises one or more computers that are programmed to perform one or more of the Computer Tasks.

In some implementations, this invention comprises one or more tangible, machine readable media, with instructions encoded thereon for one or more computers to perform one or more of the Computer Tasks. In some implementations, these one or more media are not transitory waves and are not transitory signals.

In some implementations, this invention comprises participating in a download of software, where the software comprises instructions for one or more computers to perform one or more of the Computer Tasks. For instance, the participating may comprise (a) a computer providing the software during the download, or (b) a computer receiving the software during the download.

Network Communication

In illustrative implementations of this invention, one or more devices (e.g., 105, 450) are configured for wireless or wired communication with other devices in a network.

For example, in some cases, one or more of these devices include a wireless module for wireless communication with other devices in a network. Each wireless module may include (a) one or more antennas, (b) one or more wireless transceivers, transmitters or receivers, and (c) signal processing circuitry. Each wireless module may receive and transmit data in accordance with one or more wireless standards.

In some cases, one or more of the following hardware components are used for network communication: a computer bus, a computer port, network connection, network interface device, host adapter, wireless module, wireless card, signal processor, modem, router, cables and wiring.

In some cases, one or more computers (e.g., 105 or a computer in smartphone 450) are programmed for communication over a network. For example, in some cases, one or more computers are programmed for network communication: (a) in accordance with the Internet Protocol Suite, or (b) in accordance with any other industry standard for communication, including any USB standard, ethernet standard (e.g., IEEE 802.3), token ring standard (e.g., IEEE 802.5), or wireless communication standard, including IEEE 802.11 (Wi-Fi®), IEEE 802.15 (Bluetooth®/Zigbee®), IEEE 802.16, IEEE 802.20, GSM (global system for mobile communications), UMTS (universal mobile telecommunication system), CDMA (code division multiple access, including IS-95, IS-2000, and WCDMA), LTE (long term evolution), or 5G (e.g., ITU IMT-2020).

Definitions

The terms "a" and "an", when modifying a noun, do not imply that only one of the noun exists. For example, a statement that "an apple is hanging from a branch": (i) does not imply that only one apple is hanging from the branch; (ii) is true if one apple is hanging from the branch; and (iii) is true if multiple apples are hanging from the branch.

"Associate" is defined above.

To compute "based on" specified data means to perform a computation that takes the specified data as an input.

To say that a current flows "between" A and B does not create any implication regarding direction of flow (i.e., from A to B, or from B to A).

"BL current" is defined above.

Non-limiting examples of a "camera" include: (a) a digital camera; (b) a digital grayscale camera; (c) a digital color camera; and (d) a video camera.

The term "comprise" (and grammatical variations thereof) shall be construed as if followed by "without limitation". If A comprises B, then A includes B and may include other things.

A digital computer is a non-limiting example of a "computer". An analog computer is a non-limiting example of a "computer". A computer that performs both analog and digital computations is a non-limiting example of a "computer". However, a human is not a "computer", as that term is used herein.

"Computer Tasks" is defined above.

"Defined Term" means a term or phrase that is set forth in quotation marks in this Definitions section.

For an event to occur "during" a time period, it is not necessary that the event occur throughout the entire time period. For example, an event that occurs during only a portion of a given time period occurs "during" the given time period.

The term "e.g." means for example.

The fact that an "example" or multiple examples of something are given does not imply that they are the only instances of that thing. An example (or a group of examples) is merely a non-exhaustive and non-limiting illustration.

Chronic fatigue is a non-limiting example of "fatigue".

The terms "Class A Condition" through "Class N Condition" are defined above. Also, "Class P Condition" and "Class Q Condition" are defined above, "Diagnostic session" means a period of time.

Unless the context clearly indicates otherwise: (1) a phrase that includes "a first" thing and "a second" thing does not imply an order of the two things (or that there are only two of the things); and (2) such a phrase is simply a way of identifying the two things, so that they each may be referred to later with specificity (e.g., by referring to "the first" thing and "the second" thing later). For example, if a device has a first socket and a second socket, then, unless the context clearly indicates otherwise, the device may have two or more sockets, and the first socket may occur in any spatial order relative to the second socket. A phrase that includes a "third" thing, a "fourth" thing and so on shall be construed in like manner.

As used herein, "food-related sinus allergy" means a sinus allergy that is caused (or exacerbated) at least in part by one or substances (e.g., allergens) in ingested food.

"Forearm" is defined above.

"For instance" means for example.

To say a "given" X is simply a way of identifying the X, such that the X may be referred to later with specificity. To say a "given" X does not create any implication regarding X. For example, to say a "given" X does not create any implication that X is a gift, assumption, or known fact.

A migraine is a non-limiting example of a "headache".

"Herein" means in this document, including text, specification, claims, abstract, and drawings.

As used herein: (1) "implementation" means an implementation of this invention; (2) "embodiment" means an embodiment of this invention; (3) "case" means an implementation of this invention; and (4) "use scenario" means a use scenario of this invention.

To say that a current is "in" a patient means that the current flows through at least a portion of the body of the patient.

The term "include" (and grammatical variations thereof) shall be construed as if followed by "without limitation".

"GB current" is defined above.
"HT current" is defined above.
"KI current" is defined above.
"Left side" is defined above.
"Leg" is defined above.
"LI current" is defined above.

As used herein, "lower back" means the portion of the back that is inferior to the transpyloric plane.

"LR current" is defined above.
"LU current" is defined above.

A physiological condition is a non-limiting example of a "medical condition", as that term is used herein.

"Meridian" means acupuncture meridian.

The term "mobile computing device" or "MCD" means a device that includes a computer, a camera, a display screen and a wireless transceiver. Non-limiting examples of an MCD include a smartphone, cell phone, mobile phone, tablet computer, laptop computer and notebook computer.

Unless the context clearly indicates otherwise, "or" means and/or. For example, A or B is true if A is true, or B is true, or both A and B are true. Also, for example, a calculation of A or B means a calculation of A, or a calculation of B, or a calculation of A and B.

"PC current" is defined above.

As used herein, "poor glycemic control" means: (a) blood glucose levels that are persistently greater than 200 mg/dl;

together with (b) glycated hemoglobin levels in the blood that are persistently greater than 9%.

"Prototype Current" is defined above.

"Prototype Current Ranges" is defined above.

"Prototype Electrical Current State" is defined above.

"Prototype Measurement Locations" is defined above.

"Prototype Medical Condition" is defined above.

"Right side" is defined above.

As used herein, the term "set" does not include a group with no elements.

"SI current" is defined above.

An electrode touching or being pressed against a conductive gel (or other conductive material) that is on a region of skin of a patient is a non-limiting example of the electrode "touching" or being "pressed against" the region of skin, as those terms are used herein.

Unless the context clearly indicates otherwise, "some" means one or more.

"SP current" is defined above.

"ST current" is defined above.

As used herein, a "subset" of a set consists of less than all of the elements of the set.

The term "such as" means for example.

"TH current" is defined above.

To say that a current flows "through" a body means that the current flows through at least a portion of the body.

To say that a machine-readable medium is "transitory" means that the medium is a transitory signal, such as an electromagnetic wave.

As used herein, "upper back" means the portion of the back that is superior to the transpyloric plane.

In the clause "HT current is above average or below average on left side", the phrase "on left side" modifies both "above average" and "below average". Likewise, other clauses with the same grammatical structure shall be construed in the same way. For instance, in the clause "LI current is average or below average on right side", the phrase "on right side" modifies both "average" and "below average".

"A xor B" means A or B but not A and B. Put differently, the term "xor" signifies an exclusive or.

Except to the extent that the context clearly requires otherwise, if steps in a method are described herein, then the method includes variations in which: (1) steps in the method occur in any order or sequence, including any order or sequence different than that described herein; (2) any step or steps in the method occur more than once; (3) any two steps occur the same number of times or a different number of times during the method; (4) one or more steps in the method are done in parallel or serially; (5) any step in the method is performed iteratively; (6) a given step in the method is applied to the same thing each time that the given step occurs or is applied to a different thing each time that the given step occurs; (7) one or more steps occur simultaneously; or (8) the method includes other steps, in addition to the steps described herein.

Headings are included herein merely to facilitate a reader's navigation of this document. A heading for a section does not affect the meaning or scope of that section.

This Definitions section shall, in all cases, control over and override any other definition of the Defined Terms. The Applicant or Applicants are acting as his, her, its or their own lexicographer with respect to the Defined Terms. For example, the definitions of Defined Terms set forth in this Definitions section override common usage and any external dictionary. If a given term is explicitly or implicitly defined in this document, then that definition shall be controlling, and shall override any definition of the given term arising from any source (e.g., a dictionary or common usage) that is external to this document. If this document provides clarification regarding the meaning of a particular term, then that clarification shall, to the extent applicable, override any definition of the given term arising from any source (e.g., a dictionary or common usage) that is external to this document. Unless the context clearly indicates otherwise, any definition or clarification herein of a term or phrase applies to any grammatical variation of the term or phrase, taking into account the difference in grammatical form. For example, the grammatical variations include noun, verb, participle, adjective, and possessive forms, and different declensions, and different tenses.

Variations

This invention may be implemented in many different ways. Here are some non-limiting examples:

In some implementations, this invention is a method comprising: (a) taking, in a diagnostic session, a set of measurements of electric current that flow between a ground electrode and a probe electrode through a patient's body, the measurements being taken in such a way that (i) different measurements in the set are taken while the probe electrode touches skin of the patient at different Prototype Measurement Locations, one location at a time, and (ii) each of the respective measurements in the set is taken while (A) the ground electrode touches skin of a hand of a forearm of the patient, and (B) the probe electrode touches skin of another limb of the patient at one of the Prototype Measurement Locations; (b) calculating, based on the set of measurements, a Prototype Electrical Current State for the diagnostic session; (c) employing a lookup table to identify a medical condition that the lookup table Associates with the Prototype Electrical Current State, which medical condition is a Prototype Medical Condition; and (d) outputting (i) a diagnosis that the patient has the medical condition, or (ii) a recommendation that the patient undergo medical testing to evaluate whether the patient has the medical condition. In some cases, the Prototype Medical Condition is a Class B Condition. In some cases, the Prototype Medical Condition is a Class M Condition. In some cases, the Prototype Medical Condition is a Class N Condition. In some cases, the Prototype Medical Condition is a Class P Condition. In some cases, the Prototype Medical Condition is a Class A Condition. In some cases, the Prototype Medical Condition is a Class C Condition. In some cases, the Prototype Medical Condition is a viral infection. In some cases, the Prototype Medical Condition is a bacterial infection. In some cases, the Prototype Medical Condition is a Class D Condition. Each of the cases described above in this paragraph is an example of the method described in the first sentence of this paragraph, and is also an example of an embodiment of this invention that may be combined with other embodiments of this invention.

In some implementations, this invention is a method comprising: (a) calculating a Prototype Electrical Current State for a diagnostic session, based on a set of measurements of electric current in a patient; (b) employing a lookup table to identify a medical condition that the lookup table Associates with the Prototype Electrical Current State, which medical condition is a Prototype Medical Condition; and (c) outputting (i) a diagnosis that the patient has the medical condition, or (ii) a recommendation that the patient undergo medical testing to evaluate whether the patient has the medical condition. In some cases, different measurements in the set were taken while: (a) the probe electrode touched skin of the patient at different Prototype Measurement Locations, one location at a time; and (b) the electric current flowed between a ground electrode and a probe electrode through the patient's body. In some cases, each of the respective measurements in the set was taken while: (a) the electric current flowed between a ground electrode and a probe electrode through the patient's body; (b) the ground electrode touched skin of a hand of a forearm of the patient; and (c) the probe electrode touched skin of another limb of the patient at a Prototype Measurement Location. In some cases, the Prototype Medical Condition is a Class B Condition, Class M Condition, Class N Condition or Class P Condition. Each of the cases described above in this paragraph is an example of the method described in the first sentence of this paragraph, and is also an example of an embodiment of this invention that may be combined with other embodiments of this invention.

In some implementations, this invention is a system comprising: (a) a current sensor that includes a ground electrode and a probe electrode; and (b) one or more computers; wherein (i) the current sensor is configured to take, during a diagnostic session, a set of measurements of electric current, in such a way that (A) the electric current being measured flows between the ground electrode and the probe electrode through a patient's body, (B) different measurements in the set are taken while the probe electrode touches skin of the patient at different Prototype Measurement Locations, one location at a time, and (C) each of the respective measurements in the set is taken while (I) the ground electrode touches skin of a hand of a forearm of the patient, and (II) the probe electrode touches skin of another limb of the patient at one of the Prototype Measurement Locations, and (ii) the one or more computers are programmed (A) to calculate, based on the set of measurements, a Prototype Electrical Current State for the diagnostic session, (B) to employ a lookup table to identify a medical condition that the lookup table Associates with the Prototype Electrical Current State, which medical condition is a Prototype Medical Condition, and (C) to output (I) a diagnosis that the patient has the medical condition, or (II) a recommendation that the patient undergo medical testing to evaluate whether the patient has the medical condition. In some cases, the ground electrode and the probe electrode are parts of a single rigid structure and are in a fixed position relative to each other. In some cases: (a) the system further comprises one or more pressure sensors that are each configured to measure pressure exerted on the ground electrode or the probe electrode; and (b) the ground electrode and the probe electrode are in fixed positions relative to each other, except for any movement due to displacement that occurs within the one or more pressure sensors. In some cases: (a) the system further comprises an electronic display screen and an audio transducer; and (b) the one or more computers are programmed to cause the screen and the audio transducer to together output an audiovisual presentation that provides information about whether the ground and probe electrodes are positioned correctly on the patient. In some cases: (a) the ground electrode and the probe electrode are parts of a single rigid structure and are in a fixed position relative to each other; and (b) the rigid structure is configured to partially surround a smartphone or other mobile computing device. In some cases, the Prototype Medical Condition is a Class B Condition, Class M Condition, Class N Condition or Class P Condition. Each of the cases described above in this paragraph is an example of the system described in the first sentence of this paragraph, and is also an example of an embodiment of this invention that may be combined with other embodiments of this invention.

Each description herein (or in the Provisional) of any method, apparatus or system of this invention describes a non-limiting example of this invention. This invention is not limited to those examples, and may be implemented in other ways.

Each description herein (or in the Provisional) of any prototype of this invention describes a non-limiting example of this invention. This invention is not limited to those examples, and may be implemented in other ways.

Each description herein (or in the Provisional) of any implementation, embodiment or case of this invention (or any use scenario for this invention) describes a non-limiting example of this invention. This invention is not limited to those examples, and may be implemented in other ways.

Each Figure, diagram, schematic or drawing herein (or in the Provisional) that illustrates any feature of this invention shows a non-limiting example of this invention. This invention is not limited to those examples, and may be implemented in other ways.

The above description (including without limitation any attached drawings and figures) describes illustrative implementations of the invention. However, the invention may be implemented in other ways. The methods and apparatus which are described herein are merely illustrative applications of the principles of the invention. Other arrangements, methods, modifications, and substitutions by one of ordinary skill in the art are also within the scope of the present invention. Numerous modifications may be made by those skilled in the art without departing from the scope of the invention. Also, this invention includes without limitation each combination and permutation of one or more of the items (including any hardware, hardware components, methods, processes, steps, software, algorithms, features, and technology) that are described herein.

What is claimed:

1. A method comprising:
(a) taking, in a diagnostic session, a set of measurements of electric current that flow between a ground electrode and a probe electrode through a patient's body, the measurements being taken in such a way that
  (i) different measurements in the set are taken while the probe electrode touches skin of the patient at different Prototype Measurement Locations, one location at a time, and
  (ii) each of the respective measurements in the set is taken while
    (A) the ground electrode touches skin of a hand of a forearm of the patient, and
    (B) the probe electrode touches skin of another limb of the patient at one of the Prototype Measurement Locations;
(b) calculating, based on the set of measurements, a Prototype Electrical Current State for the diagnostic session;
(c) employing a lookup table to identify a medical condition that the lookup table associates with the Prototype Electrical Current State, wherein the medical condition is a Prototype Medical Condition; and
(d) outputting
  (i) a diagnosis that the patient has the medical condition, or
  (ii) a recommendation that the patient undergo medical testing to evaluate whether the patient has the medical condition.

2. The method of claim 1, wherein the Prototype Medical Condition is a Class B Condition.

3. The method of claim 1, wherein the Prototype Medical Condition is a Class M Condition.

4. The method of claim 1, wherein the Prototype Medical Condition is a Class N Condition.

5. The method of claim 1, wherein the Prototype Medical Condition is a Class P Condition.

6. The method of claim 1, wherein the Prototype Medical Condition is a Class A Condition.

7. The method of claim 1, wherein the Prototype Medical Condition is a Class C Condition.

8. The method of claim 1, wherein the Prototype Medical Condition is a viral infection.

9. The method of claim 1, wherein the Prototype Medical Condition is a bacterial infection.

10. The method of claim 1, wherein the Prototype Medical Condition is a Class D Condition.

11. A method comprising:
- (a) calculating a Prototype Electrical Current State for a diagnostic session, based on a set of measurements of electric current in a patient;
- (b) employing a lookup table to identify a medical condition that the lookup table associates with the Prototype Electrical Current State, wherein the medical condition is a Prototype Medical Condition; and
- (c) outputting
  - (i) a diagnosis that the patient has the medical condition, or
  - (ii) a recommendation that the patient undergo medical testing to evaluate whether the patient has the medical condition.

12. The method of claim 11 wherein different measurements in the set were taken while:
- (a) a probe electrode touched skin of the patient at different Prototype Measurement Locations, one location at a time; and
- (b) the electric current flowed between a ground electrode and the probe electrode through the patient's body.

13. The method of claim 11, wherein each of the respective measurements in the set was taken while:
- (a) the electric current flowed between a ground electrode and a probe electrode through the patient's body;
- (b) the ground electrode touched skin of a hand of a forearm of the patient; and
- (c) the probe electrode touched skin of another limb of the patient at a Prototype Measurement Location.

14. The method of claim 11, wherein the Prototype Medical Condition is a Class B Condition, Class M Condition, Class N Condition or Class P Condition.

15. A system comprising:
- (a) a current sensor that includes a ground electrode and a probe electrode; and
- (b) one or more computers; wherein
  - (i) the current sensor is configured to take, during a diagnostic session, a set of measurements of electric current, in such a way that
    - (A) the electric current being measured flows between the ground electrode and the probe electrode through a patient's body,
    - (B) different measurements in the set are taken while the probe electrode touches skin of the patient at different Prototype Measurement Locations, one location at a time, and
    - (C) each of the respective measurements in the set is taken while
      - (I) the ground electrode touches skin of a hand of a forearm of the patient, and
      - (II) the probe electrode touches skin of another limb of the patient at one of the Prototype Measurement Locations, and
  - (ii) the one or more computers are programmed
    - (A) to calculate, based on the set of measurements, a Prototype Electrical Current State for the diagnostic session,
    - (B) to employ a lookup table to identify a medical condition that the lookup table associates with the Prototype Electrical Current State, wherein the medical condition is a Prototype Medical Condition, and
    - (C) to output
      - (I) a diagnosis that the patient has the medical condition, or
      - (II) a recommendation that the patient undergo medical testing to evaluate whether the patient has the medical condition.

16. The system of claim 15, wherein the ground electrode and the probe electrode are parts of a single rigid structure and are in a fixed position relative to each other.

17. The system of claim 15, wherein:
- (a) the system further comprises one or more pressure sensors that are each configured to measure pressure exerted on the ground electrode or the probe electrode; and
- (b) the ground electrode and the probe electrode are in fixed positions relative to each other, except for any movement due to displacement that occurs within the one or more pressure sensors.

18. The system of claim 15, wherein:
- (a) the system further comprises an electronic display screen and an audio transducer; and
- (b) the one or more computers are programmed to cause the screen and the audio transducer to together output an audiovisual presentation that provides information about whether the ground and probe electrodes are positioned correctly on the patient.

19. The system of claim 15, wherein:
- (a) the ground electrode and the probe electrode are parts of a single rigid structure and are in a fixed position relative to each other; and
- (b) the rigid structure is configured to partially surround a smartphone or other mobile computing device.

20. The system of claim 15, wherein the Prototype Medical Condition is a Class B Condition, Class M Condition, Class N Condition or Class P Condition.

* * * * *